(12) United States Patent
Amalaradjou

(10) Patent No.: US 11,497,197 B2
(45) Date of Patent: Nov. 15, 2022

(54) METHODS FOR ENHANCING POULTRY GROWTH AND PERFORMANCE

(71) Applicant: University of Connecticut, Farmington, CT (US)

(72) Inventor: Mary Anne Amalaradjou, Storr, CT (US)

(73) Assignee: UNIVERSITY OF CONNECTICUT, Farmington, CT (US)

(*) Notice: Subject to any disclaimer, the term of this patent is extended or adjusted under 35 U.S.C. 154(b) by 580 days.

(21) Appl. No.: 16/515,856

(22) Filed: Jul. 18, 2019

(65) Prior Publication Data

US 2020/0022339 A1 Jan. 23, 2020

Related U.S. Application Data

(60) Provisional application No. 62/699,945, filed on Jul. 18, 2018.

(51) Int. Cl.
*A01K 45/00* (2006.01)
*A01K 29/00* (2006.01)
(Continued)

(52) U.S. Cl.
CPC .......... *A01K 45/007* (2013.01); *A01K 29/005* (2013.01); *A23K 10/18* (2016.05); *A61K 35/744* (2013.01)

(58) Field of Classification Search
CPC .... A01K 45/007; A01K 29/005; A23K 10/18; A61K 35/741; A61K 35/744;
(Continued)

(56) References Cited

U.S. PATENT DOCUMENTS 4,458,630 A * 7/1984 Sharma ................ A01K 45/007
119/6.8
5,206,015 A * 4/1993 Cox ..................... A61K 35/741
119/6.6
(Continued)

FOREIGN PATENT DOCUMENTS

CA 2761442 A1 * 11/2010 ............... A61P 37/08
CA 2353544 C * 2/2011 ........... A61K 35/745
(Continued)

OTHER PUBLICATIONS

El-Dayem et al., "Effect of Using Lactobacillus Acidophilus on E.coli Causing Embryonic Death and Low Hatchability in Balady Hatcheries at Dakahalia Governorate", Assiut Veterinary Medical Journal, vol. 59, No. 138, Jul. 2013, pp. 170-176.
(Continued)

*Primary Examiner* — Ebony E Evans
(74) *Attorney, Agent, or Firm* — Cantor Colburn LLP

(57) ABSTRACT

Methods for enhancing embryonic and post-hatch growth and performance of poultry by administration of a probiotic composition, such as a composition containing a mixture of one or more bacterial cultures, to the surface of the shells of fertilized eggs prior to setting. Optionally, the method further includes administration of the same probiotic composition at the same concentration to chicks hatched from the eggs that had received the topical in ovo administration to the shell. The probiotic composition is administered to the chicks orally, such as in feed.

18 Claims, 17 Drawing Sheets

(51) Int. Cl.
*A23K 10/18* (2016.01)
*A61K 35/744* (2015.01)

(58) Field of Classification Search
CPC .... A61K 35/745; A61K 35/747; A61K 35/74; A61K 38/00; A61K 36/06
USPC .......................................................... 119/6.8
See application file for complete search history.

(56) References Cited

U.S. PATENT DOCUMENTS

| | | | |
|---|---|---|---|
| 5,722,342 A * | 3/1998 | Line | A01K 45/007 |
| | | | 119/6.8 |
| 6,244,214 B1 | 6/2001 | Hebrank | |
| 6,410,016 B2 | 6/2002 | Maruta et al. | |
| 6,660,294 B2 | 12/2003 | Maruta et al. | |
| 2010/0186674 A1 * | 7/2010 | Cahill, Jr. | A01K 33/00 |
| | | | 119/6.8 |
| 2011/0126767 A1 * | 6/2011 | Lahav | A61P 43/00 |
| | | | 119/6.8 |
| 2014/0328815 A1 | 11/2014 | Ware | |
| 2019/0269608 A1 * | 9/2019 | Clevers | A61K 8/99 |

FOREIGN PATENT DOCUMENTS

| | | | | |
|---|---|---|---|---|
| EP | 1552848 A1 * | 7/2005 | | A61P 33/02 |
| WO | WO-9800151 A2 * | 1/1998 | | A61K 36/06 |

OTHER PUBLICATIONS

PCT Publication No. PCT/US2019/042410, International Search Report and Written Opinion, dated Oct. 2, 2019, 6 pages.

Amalaradjou, "Pre-Harvest Approaches to Improve Poultry Meat Safety", Food Safety in Poultry Meat Production, Jan. 2019, pp. 95-122.

Dilworth, et al., "Lactobacillus Cultures in Broiler Diets", Poultry Science, vol. 57, 1978, p. 1101.

Guillen, "Microbial Species Characteristics and Selection", Direct-Fed Microbials and Prebiotics for Animals, 2011, pp. 27-33.

Molenaar, et al., "Relationship Between Hatchling Length and Weight on Later Productive Performance in Broilers", World's Poultry Science Journal, vol. 64, No. 4, Dec. 2008, pp. 599-604.

Mutus, et al., "The Effect of Dietary Probiotic Supplementation on Tibial Bone Characteristics and Strength in Broilers", Poultry Science, vol. 85, No. 9, Sep. 2006, pp. 1621-1625.

Odea, et al., "Investigating the Effects of Commercial Probiotics on Broiler Chick Quality and Production Efficiency", Poultry Science, vol. 85, No. 10, Oct. 2006, pp. 1855-1863.

Pelicano, et al., "Effect of Different Probiotics on Broiler Carcass and Meat Quality", Brazilian Journal of Poultry Science, vol. 5, No. 3, Sep.-Dec. 2003, pp. 207-214.

Pelicano, et al., "Productive Traits of Broiler Chickens Fed Diets Containing Different Growth Promoters", Brazilian Journal of Poultry Science, vol. 6, No. 3, Jul.-Sep. 2004, pp. 177-182.

Pender, et al., "Effects of in Ovo Supplementation of Probiotics on Performance and Immunocompetence of Broiler Chicks to an Eimeria Challenge", Beneficial Microbes, vol. 7, No. 5, Oct. 11, 2016, pp. 699-705.

Reed, et al., "Poor Maternal Nutrition Inhibits Muscle Development in Ovine Offspring", Journal of Animal Science and Biotechnology, vol. 5, No. 43, Sep. 2014, 11 pages.

Sashihara, et al., "An Analysis of the Effectiveness of Heat-Killed Lactic Acid Bacteria in Alleviating Allergic Diseases", Journal of Dairy Science, vol. 89, No. 8, Aug. 2006, pp. 2846-2855.

Uni, et al., "In Ovo Feeding Improves Energy Status of Late-Term Chicken Embryos", Poultry Science, vol. 84, No. 5, Jun. 2005, pp. 764-770.

Watkins, et al., "Drinking Water Treatment with a Commercial Preparation of a Concentrated Lactobacillus Culture for Broiler Chickens", Poultry Science, vol. 63, No. 8, Aug. 1984, pp. 1671-1673.

Zammit, et al., "The Skeletal Muscle Satellite Cell: the Stem Cell that Came in from the Cold", Journal of Histochemistry & Cytochemistry, vol. 54, No. 11, Nov. 2006, pp. 1177-1191.

* cited by examiner

EC: Egg control (no probiotic supplementation)
IO: *In ovo* probiotic supplementation
IOIF: *In ovo* and in-feed probiotic supplementation EC: Egg control (no probiotic supplementation)
IO: *In ovo* probiotic supplementation
IOIF: *In ovo* and in-feed probiotic supplementation EC: Egg control (no probiotic supplementation)
IO: *In ovo* probiotic supplementation
IOIF: *In ovo* and in-feed probiotic supplementation Data are represented as average ± SEM; *Means are significantly different at $P \leq 0.05$ Data are represented as average ± SEM; *Treatments are significantly different from the control at $P \leq 0.05$ Control: Egg control (no probiotic supplementation)
LP: In ovo and in-feed probiotic supplementation with *L. paracasei*
IOIF: In ovo and in-feed probiotic supplementation with *L. rhamnosus*

Control: Egg control (no probiotic supplementation)
B13076: *In ovo* and in-feed probiotic supplementation with *L. paracasei*
B442: *In ovo* and in-feed probiotic supplementation with *L. rhamnosus*

* Indicates significant difference between the treatment groups (p<0.05)

* Indicates significant difference between the treatment groups (p<0.05)

* Indicates the significant difference between the treatment groups (p<0.05)

* Indicates treatments are significantly different from the control ($p<0.05$)
EC: Egg control (no probiotic supplementation)
IF: in-feed probiotic supplementation
IO: *In ovo* probiotic supplementation
IOIF: *In ovo* and in-feed probiotic supplementation

* Indicates treatments are significantly different from the control ($p<0.05$)

EC: Egg control (no probiotic supplementation)
IF: in-feed probiotic supplementation
IO: *In ovo* probiotic supplementation
IOIF: *In ovo* and in-feed probiotic supplementation

Fig. 16

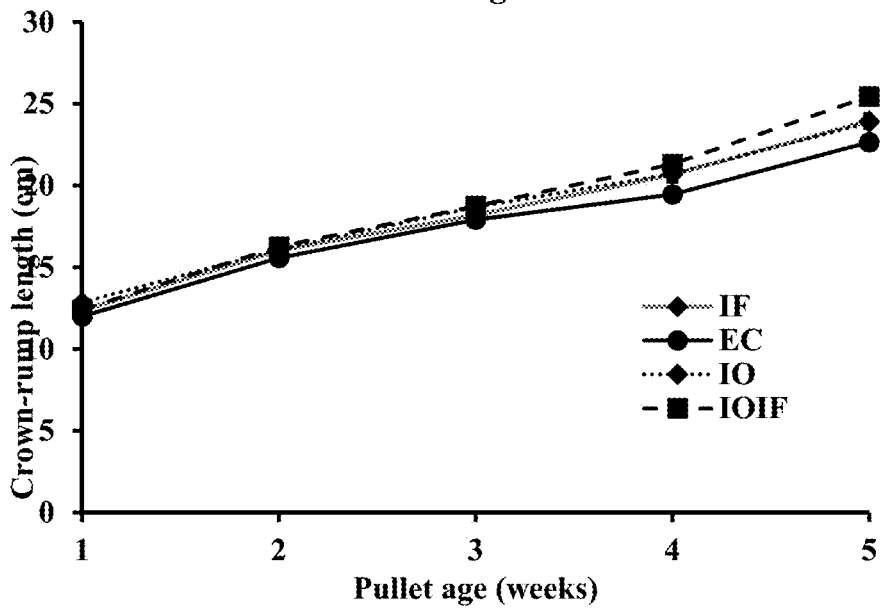

EC: Egg control (no probiotic supplementation)
IF: in-feed probiotic supplementation
IO: *In ovo* probiotic supplementation
IOIF: *In ovo* and in-feed probiotic supplementation

Fig. 17

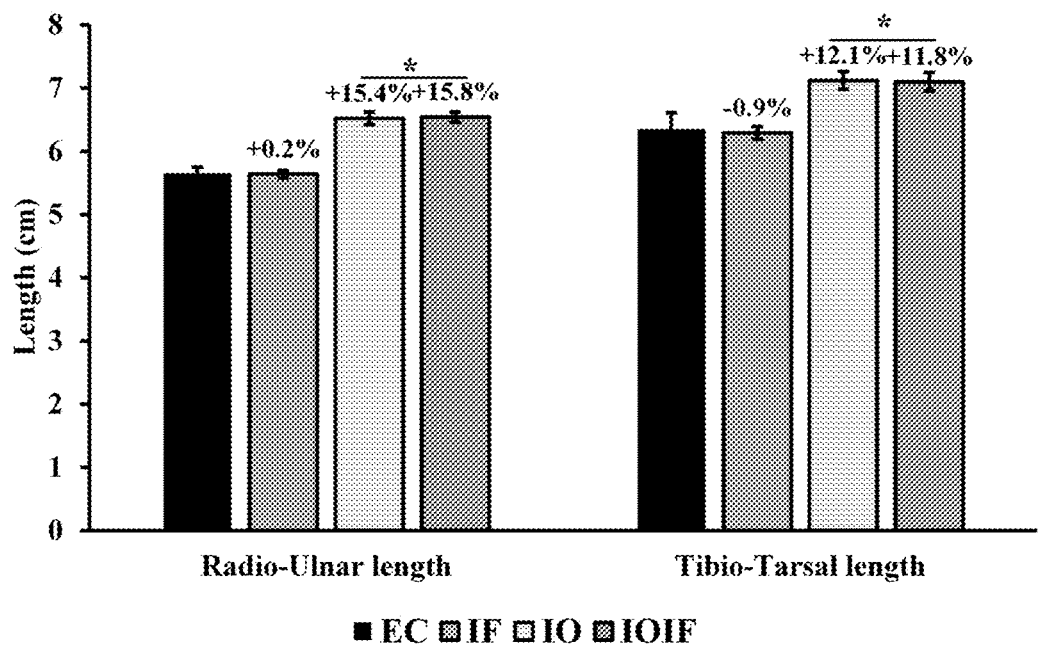

* Indicates treatments are significantly different from the control ($p<0.05$)
  EC: Egg control (no probiotic supplementation)
  IF: in-feed probiotic supplementation
  IO: *In ovo* probiotic supplementation
  IOIF: *In ovo* and in-feed probiotic supplementation a-b; Indicates treatments are significantly different from the control ($p<0.05$) for each parameter

Fig. 20a

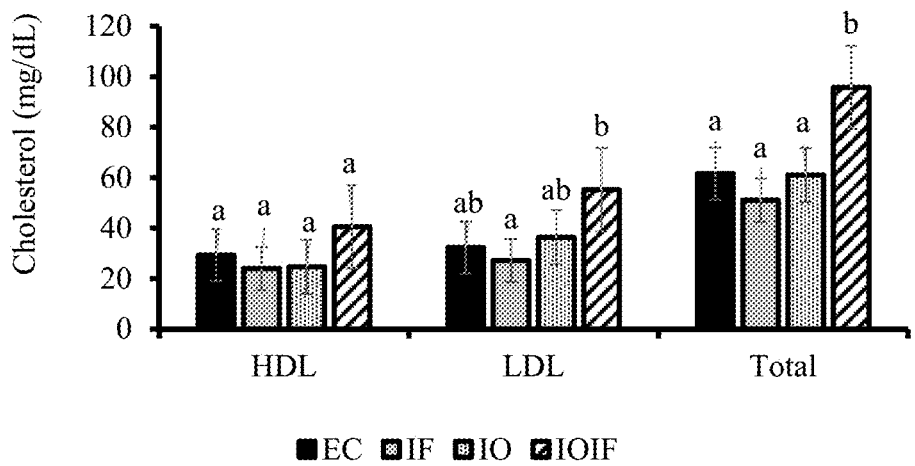

a-b: Indicates treatments are significantly different from the control ($p<0.05$) for each parameter.
EC: Egg control (no probiotic supplementation)
IF: in-feed probiotic supplementation
IO: *In ovo* probiotic supplementation
IOIF: *In ovo* and in-feed probiotic supplementation

Fig. 20b

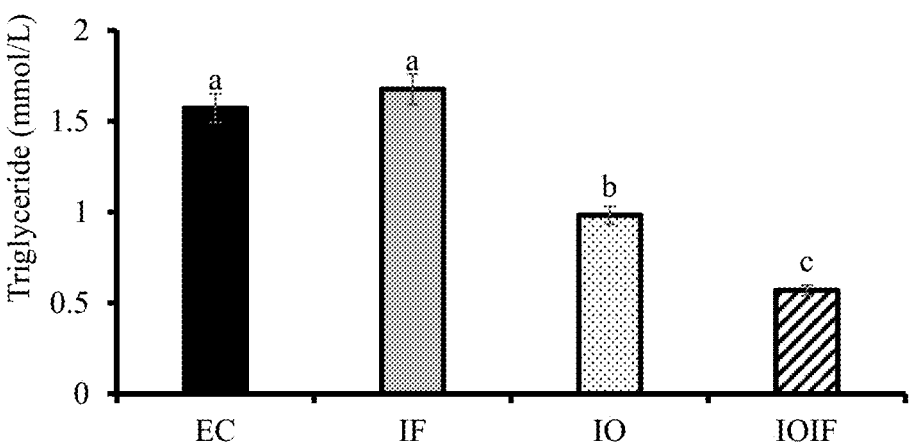

a-c; Indicates treatments are significantly different from the control ($p<0.05$)
EC: Egg control (no probiotic supplementation)
IF: in-feed probiotic supplementation
IO: *In ovo* probiotic supplementation
IOIF: *In ovo* and in-feed probiotic supplementation EC: Egg control (no probiotic supplementation)
IF: in-feed probiotic supplementation
IO: *In ovo* probiotic supplementation
IOIF: *In ovo* and in-feed probiotic supplementation Data are represented as mean ± SEM. a-c: Different superscripts indicate significant difference from control within each sampling time.

Data are represented as mean ± SEM. a-c: Different superscripts indicate significant difference from control within each sampling time.

Data are represented as mean ± SEM. [a-d]: Different superscripts indicate significant difference from control within each sampling time.

METHODS FOR ENHANCING POULTRY GROWTH AND PERFORMANCE

CROSS-REFERENCE TO RELATED APPLICATIONS

This application claims priority to U.S. Provisional Patent Application No. 62/699,945, filed on Jul. 18, 2018, the entire contents of each of which are incorporated by reference herein.

STATEMENT AS TO RIGHTS TO INVENTIONS MADE UNDER FEDERALLY SPONSORED RESEARCH AND DEVELOPMENT

This invention was made in part with government support under Contract No. GNE 16-128-29994, awarded by the USDA, Northeast SARE Graduate Student Award, a subaward of USDA/NIFA Grant 2015-38640-23777. The government has certain rights in the invention.

BACKGROUND

Field of the Invention

The present invention relates to a method for enhancing the growth of poultry by administration of probiotics. More particularly, the invention relates to a method for improving embryonic and post-hatch poultry growth and performance.

Background

Over the last few decades, increased consumer awareness and demand for a healthy diet have highlighted the significant role of poultry products as a source of high-quality protein for human consumption. In order to meet this ever-growing demand, the poultry industry adopted intensive rearing practices which led to a tremendous increase in meat and egg production. In fact, the United States is the largest producer and second largest exporter of poultry meat in the world (USDA 2016). In the last year, the US poultry industry produced around 8.6 billion broilers accounting for 53.4 billion pounds (live weight) with a monetary value of 28.7 billion dollars (USDA NASS, 2016). Similarly, with reference to egg production, the United States is a major producer of eggs in the world second only to mainland China (USDA 2016). Current data indicate that the US Table egg flock size consists of 313 million layers producing 7.55 billion eggs (USDA 2016). This tremendous growth and production obtained by the poultry industry have been a result of planned genetic selection of poultry breeds targeting higher feed conversion efficiency and performance.

The use of antibiotics as a dietary supplement has increased the incidence of antibiotic-resistant pathogens, accumulation of antibiotic residues in various poultry products intended for human consumption, and the alteration of poultry microbiome which can affect poultry performance. Further, the continued use of antibiotics as prophylactics and growth promoters in food animals has been linked to the increase in emergence of antibiotic-resistant pathogens and their implications to human health. Hence FDA has issued a directive limiting the use of antibiotics in livestock and poultry production. This has led to an intensified effort to identify and develop efficient alternate growth promoters for food animals.

Among the different alternatives used, probiotics have been demonstrated to elicit several of the growth-promoting effects associated with AGPs. These microorganisms promote animal health and production efficiency through multiple mechanisms including i) maintenance of healthy gut microflora, ii) enhanced feed intake and digestion, iii) prevention of pathogen survival and colonization and iv) production of antimicrobial metabolites. Towards this, several researchers have demonstrated the potential for dietary supplementation of probiotics in day-old chicks on improving growth performance in chicken. In-feed supplementation of probiotics has also demonstrated growth promoting abilities associated with an increase in growth and performance in chicken. Pelicano et al., *Brazilian Journal of Poultry Science*. 2004; 6:177-182 observed improved feed conversion ratio in broilers who received commercial probiotics with one of these combinations, the first probiotic was composed of *Bacillus subtilis* (150 g/ton feed) and the second included *Lactobacillus acidophilus, L. casei, Streptococcus lactis, S. faecium, Bifidobacterium bifidum* and *Aspergillus oryzae* (1 kg/ton feed) regardless of the composition. Besides promoting growth, studies have also demonstrated that supplementation of probiotics significantly improved carcass quality. However, studies on early in ovo administration of probiotics in the chicken embryo are lacking.

SUMMARY

Methods for enhancing the growth and/or performance of poultry are described in which a probiotic composition is administered to a fertilized, unhatched poultry egg after laying and prior to setting. In some embodiments, the probiotic composition is administered to the egg more than once and at predetermined time intervals after laying. Administration is prior to setting, and also during setting. Optionally, administration is also after setting (hatching). For example, a first administration is administered before setting and a last administration is administered prior to hatching. In some embodiments, the probiotic composition is administered once before setting and between one and five times during setting, but before hatching. In other embodiments, the probiotic composition is administered once before setting, between 1 and 5 times during setting and between 1 and every day to a chick hatched from the egg. For example, the probiotic composition is administered once topically before setting, between 1 and 5 times topically during setting and orally between one and every day to the chick (following hatch) as an in-feed supplement.

The probiotic composition is a microorganism such as a bacterium or fungus or a combination thereof. Suitable bacteria or fungi are *Bacillus, Lactobacillus, Lactococcus, Propionibacterium, Enterococcus, Pediococcus, Baterioides, Bifidobacterium, Saccharomyces* and *Aspergillus*.

Optionally, the method further includes administration of the same probiotic composition at the same concentration, or an alternative probiotic composition and/or an alternative concentration, to chicks hatched from the eggs that had received the topical in ovo administration. The probiotic composition is administered to the chicks orally, such as in feed that is fed to the chicks.

Administration of the probiotic composition to poultry eggs results in the formation of chick embryos exhibiting enhanced embryonic growth as evidenced by measurable parameters such as higher embryo weight and/or longer crown rump length when compared with control poultry eggs (to which the probiotic composition was not administered). In some embodiments, administration of the probiotic composition to poultry eggs results in the formation of chick embryos exhibiting enhanced performance such as increased yolk sac carbohydrate levels and/or increased hatchability when compared with control poultry eggs.

Furthermore, administration of the probiotic composition to chicks hatched from the eggs treated in accordance with the method described herein results in enhanced post-hatch growth such as an increase over control in post-hatch weight, ready-to-cook weight, breast weight and bone length when compared against controls.

In some embodiments, further treatment of the hatched chicks by administration of the probiotic composition orally, as described above, result in poultry having an even greater enhanced effect on growth when compared to in ovo treatment alone.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 16 is a graph showing crown-rump length in layer chicks (pullet) over time.

FIG. 17 is a bar graph showing radio-ulna and tibio-tarsal length in pullets at week 5.

FIG. 20a is a bar graph showing serum cholesterol level in pullets on week 5.

FIG. 20b is a bar graph showing serum triglyceride level in pullets on week 5.

Figure 1:
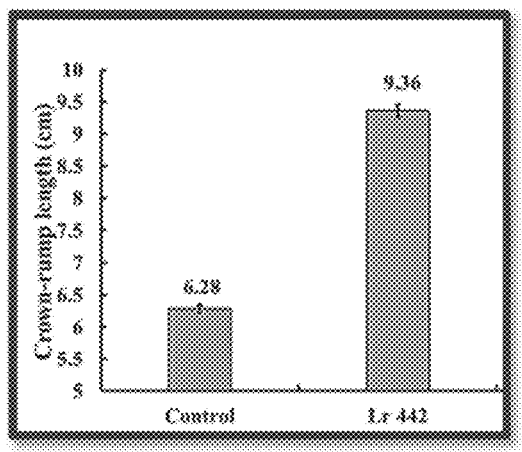
FIG. 1 is a bar graph showing Crown-rump length of layer embryos on day 18 of incubation versus control.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word "may" is used in a permissive sense (i.e., meaning having the potential to), rather than the mandatory sense (i.e., meaning must). Similarly, the words "include," "including," and "includes" mean including, but not limited to. Additionally, as used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "setting" as used herein means placing eggs in an incubator.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to "one embodiment" or "an embodiment." The appearances of the phrases "in one embodiment" or "in an embodiment" do not necessarily refer to the same embodiment, although embodiments that include any combination of the features are generally contemplated, unless expressly disclaimed herein. Particular features, structures, or characteristics may be combined in any suitable manner consistent with this disclosure.

Methods for enhancing the growth and/or performance of poultry are provided herein. The poultry for which the methods described herein are employed are intended to be used as a food product for human or animal consumption, and therefore include protein food sources such as chicken, duck and ostrich poultry. Chickens include layers, who produce eggs that are consumed as food, and broilers, who are consumed directly as a food source.

In accordance with the method, a probiotic composition is administered to a fertilized, unhatched poultry egg. The probiotic composition is administered to the egg prior to incubation (setting). In some embodiments, the probiotic composition is administered to the egg more than once and at predetermined time intervals after laying, wherein a first administration is administered before setting and a last administration is administered prior to hatching. In some embodiments, the probiotic composition is administered once before setting and between 1 and 5 times during setting, but before hatching. In some embodiments, the probiotic composition is administered before setting, during setting and after hatching. For example, the probiotic composition is administered at least once, on predetermined days or every day to chicks (following hatch) as an in-feed supplement.

The probiotic composition is administered to the egg topically, such as by applying a liquid solution or an aerosol of a liquid solution of the probiotic composition to the surface of the egg, i.e. the egg shell. In some embodiments, 50 to 2000 of the probiotic composition at a concentration of approximately 7 to 8 log CFU (colony forming units) per egg is administered at each administration. The concentration is sufficient to stimulate embryonic growth, without causing infection or other adverse pathogenic effects.

In some embodiments, the probiotic composition is an aerosol composition that is sprayed onto the surface of the egg. The egg may be stationary during the administration or in a state of movement, such as rolling, during the administration to facilitate coating.

The probiotic composition is a microorganism such as a bacterium or fungus. Suitable bacterial and fungal genera include *Bacillus, Lactobacillus, Lactococcus, Propionibacterium, Enterococcus, Pediococcus, Bacteroides, Bifidobacterium, Aspergillus* and *Saccharomyces*. For example, the bacteria or fungi in the probiotic composition are one or more of *Bacillus subtilis, Lactobacillus acidophilus, L. casei, L. paracasei, L. rhamnosus, Lactococcus lactis, Enterococcus faecium, Propionibacterium shermanii, Pediococcus pentosaceus, Bacteroides amylophilus, Bifidobacterium bifidum, Aspergillus oryzae* and *Saccharomyces cerevisiae*. In some embodiments, the probiotic composition contains a mixture of cultures such as *Bacillus subtilis, Lactobacillus acidophilus, L. casei, L. paracasei, L rhamnosus, Lactococcus lactis, Bifidobacterium bifidum Aspergillus oryzae* and *Saccharomyces cerevisiae*. In some embodiments, the probiotic composition is a solution containing a mixture of *Lactobacillus paracasei* and *L. rhamnosus*. In other embodiments, the mixture contains equal amounts of *Lactobacillus paracasei* and *L. rhamnosus*. In some embodiments the probiotic composition is a lactic acid bacterium or a mixture of lactic acid bacteria. Other probiotic useful in the probiotic compositions and methods described herein are described and can be identified in Guillen, L. M. (2011) Microbial species characteristics and selection. In R. R. Callaway & S. C. Ricke (Eds.), DIRECT-FED MICROBIALS AND PREBIOTICS FOR ANIMALS: SCIENCE AND MECHANISMS OF ACTION (pp. 27-33). Springer Science & Business Media and in Amalaradjou, M. S. (2019). Pre-harvest approaches to improve poultry meat safety. In K. Venkitanarayanan, S. Thakur & S. C. Ricke (Eds.). FOOD SAFETY IN POULTRY MEAT PRODUCTION (pp. 95-122). Springer Nature Switzerland AG.

Optionally, the method further includes administration of the same probiotic composition at the same concentration, or an alternative probiotic composition, to chicks hatched from the eggs that had received the topical in ovo administration to the egg shell as described above. The probiotic composition is administered to the chicks orally. In some embodiments, the probiotic composition is combined with feed that is fed to the chicks.

When the method is employed, as described above, and the probiotic composition is administered to poultry eggs, the embryos exhibit enhanced embryonic growth as evidenced by measurable parameters such as higher embryo weight, longer crown rump length. In addition, administration of the probiotic composition to poultry eggs, the embryos exhibit enhanced performance such as increased yolk sac carbohydrate levels and/or increased hatchability. In addition, upon administration of the probiotic composition to poultry eggs, the embryos exhibit enhanced performance such as increased yolk sac carbohydrate levels and/or increased hatchability.

Furthermore, chicks hatched from the eggs treated in accordance with the method described herein exhibit enhanced post-hatch growth such as an increase over control in post-hatch weight, ready-to-cook weight, breast weight and bone length.

In some embodiments where the hatched chicks are further treated by administration of the probiotic composition orally, as described above, the poultry have an even greater enhanced effect on growth when compared to in ovo treatment alone.

The disclosure will now be described by way of reference only to the following non-limiting examples. It should be understood, however, that the examples following are illustrative only, and should not be taken in any way as a restriction on the generality of the invention described herein.

EXAMPLES

Example 1: Early (in Ovo) and Sustained Application of Probiotics Improves Embryonic and Post-Hatch Growth in Layers and Performance in Broilers This study analyzed application of probiotics in ovo followed by administration of probiotics in feed to newly hatched chicks to determine effects on growth in poultry layers and broilers.

Methods

LAB Culture Conditions and Preparation of Probiotic Spray

Probiotic strains, *L. paracasei* DUP-13076, and *L. rhamnosus* NRRL-B-442 were obtained from Dr. Bhunia, Food Science Department, Purdue University and the USDA NRRL culture collection, respectively. Each strain was cultured separately in 10 ml of de Mann, Rogosa, Sharpe broth (MRS) under anaerobic conditions at 37° C. for 24 h. The cells were then sedimented by centrifugation (3600×g for 15 min), washed twice with sterile phosphate buffered saline (PBS, pH 7.0), and resuspended in 10 ml PBS. The approximate bacterial count in each culture was determined spectrophotometrically. Equal portions from each of the strains were combined to make a two-strain probiotic cocktail. The bacterial population in the two-strain mixture was determined by plating 0.1-ml portions of appropriate dilutions on MRS agar, followed by anaerobic incubation at 37° C. for 24 h. Appropriate dilutions of the two-strain mixture in PBS were used to obtain the desired level of inoculum (9 log CFU).

Experimental Design

Layers:

Freshly laid fertile Lowman White Leghorn eggs were collected from the University of Connecticut poultry farm and randomly assigned to the following 3 groups. The 3 treatment groups were: i) Egg control (EC; PBS only), ii) In ovo probiotic cocktail treatment (IV) on eggs (in ovo only; eggs were sprayed with 200 µl (~9 log CFU/egg) probiotic cocktail on days 1, 3, 7, 10, 14, and 18 of incubation) and iii) In ovo+ in-feed probiotic cocktail supplementation [Eggs will be sprayed with 200 µl (~9 log CFU/egg) probiotic, followed by in-feed supplementation (~9 log CFU/kg of feed) following hatch until sacrifice (IOIF)]. Experimental groups are summarized in Table 1.

TABLE 1

Treatment groups for layer trial

| Treatment groups (Pre-hatch) | Treatment groups (Post-hatch) | Description |
| --- | --- | --- |
| Control | EC | No treatment applied |
| Probiotic | IO | Probiotic cocktail applied in ovo only |
|  | IOIF | Probiotic cocktail applied both in-feed and in ovo |

1. Egg Treatment, Incubation, and Sampling

Eggs were weighed and kept at room temperature overnight. Eggs in group 2 (IO) and 3 (IOIF) were sprayed with 200 µl of the probiotic cocktail (~9 log CFU/egg) while eggs in group 1 (EC) and 3 (IF) were sprayed with PBS (solvent control; 200 µl of PBS/egg) using an atomizer. The sprayed eggs were then incubated in a thermostat incubator (2362N HovaBator, GQF Manufacturing Company Inc., GA) with an automatic egg turner (1611 egg turner with 6 universal racks, GQF Manufacturing Company Inc.), temperature and humidity control for 18 days at 37.8° C. and 55% relative humidity. During this period, ten eggs per treatment were sampled on days 1, 7, 14 and 18. These eggs were weighed, dipped in 50 ml PBS, rubbed for one minute, and the surviving probiotic population were enumerated by plating on MRS agar.

2. Morphometry of Embryos

In addition to probiotic enumeration, morphometric measurements including organ, yolk sac, yolk-free embryo mass and embryo weights, crown-rump length, tarsal length, tibial length and the length of the third digit were measured during the embryonic period.

3. Hatchability and Post-Hatch Performance Parameters

On day 18, the remaining eggs were sprayed with probiotics or PBS and transferred to the hatcher and held at 37.8° C. and 65% relative humidity for 3 days or until hatch. On the day of hatch (day 21), percent hatchability was recorded, and hatchlings were weighed prior to placement on floor pens. Ten hatchlings from each treatment group were sacrificed, and morphometric measurements were performed as described above. Blood was collected in non-heparinized vials to obtain serum for serum lipid analysis. Entire gizzard, liver, breast, and thigh were collected, weighed and expressed relative to body weight.

4. Chicken Diet, and Management

Day-old chicks were transferred to floor pens, and feed/water was administered ad libitum for the entire 5 week experimental period. All birds were grouped in separate pens depending on the treatment type. Birds of each group received feed supplementation similar to the treatment they obtained while they were embryos (Table 1). For the in-feed supplementation, the probiotic cocktail was prepared as described previously. The appropriate volume of the cocktail culture was added to the feed and mixed thoroughly to obtain the desired concentration (~9 log CFU/g) in the feed.

5. Body Weight and Feed Conversion Ratio

Prior to feeding, individual body weights were obtained on week 1, 2, 3, 4 and 5. Feed consumed was recorded daily on per pen basis, the uneaten feed was collected once daily before morning feeding and feed conversion ratio was calculated as the proportion of live weight over the feed consumed.

6. Organ Weights and Carcass Yield Percentages

On weeks 1, 2, 3, 4 and 5, ten birds from each treatment group were sacrificed. Internal organs, gizzard, heart, liver, breast, and thigh were collected. Both absolute and relative organ weight were calculated. Head and feet of the bird were removed, followed by de-feathering, and evisceration so that the carcass was in a ready to cook (RTC) state. RTC carcass weight was measured and expressed as a percentage of live body weight.

7. Statistical Analysis

A completely randomized design with factorial treatment structure was followed. For the first part of the experiment involving the eggs, the experimental unit was a Hovabator™ that received different treated-diets (100 eggs per incubator), and the sampling unit was the egg. For the morphometric measurements, the factors includes 3 treatments (control, TO, IOIF), 6 parameters (organ and embryo weight, crown-rump length, tarsal length, tibial length and the length of the third digit), and 4 time points (day 1, 7, 14 and 18). For the second part of the study involving hatchling/chicken, the experimental unit was the pen of chickens that received different diets (60 birds/pen), and the sampling unit was the bird. In the chicken performance data, the factors included the 4 treatments, 4 parameters (body weight, carcass weight, feed intake, feed conversion rate), and 5 time points (week 1, 2, 3, 4 and 5). In organ weight data, the factors included 4 treatments, 5 samples (gizzard, heart, liver, breast and thigh), and 5 time points (week 1, 2, 3, 4 and 5). The proc-MIXED and proc-PLM procedures of the SAS (SAS Institute Inc. Cary, N.C.) were used for the analysis. When appropriate, means comparisons were made using the least square means and differences between least square means were separated. The significance was considered at p<0.05.

Results:

Effect on embryonic growth on day 18: Results from this study demonstrated that early probiotic supplementation significantly increased (P≤0.05) all tested parameters in the treatment groups when compared with the control (Table 2). Of interest is the significant increase in embryo weight (32 g vs 26 g) and crown rump length (9.3 cm vs 6.2 cm) in treatment groups compared to the control (Table 2, FIG. 1). This is noteworthy since longer chicks have been associated with better use of egg nutrients and higher post hatch growth. In addition, there was no significant difference in the yolk-sac weight or its percentage relative to original egg weight between the different groups (Table 2). This suggests that the observed increase in embryo weight in the treatment groups (in the absence of a proportionate decrease in yolk sac mass) may be attributed to better nutrient utilization in the probiotic group as opposed to the control (group 1). Further, we did not observe any gross morphological changes in the internal organs. Additionally, probiotic supplementation did not exert any adverse effects on embryo viability.

TABLE 2

Biometric measurements of layer embryos (d 18 of incubation) treated with different probiotic strains

| Parameters | Treatment groups | |
| --- | --- | --- |
| | Control | IO |
| Embryo weight (g) (YFBM) | 26.20 ± 0.81$^a$ | 32.29 ± 1.75$^b$ |
| % Embryo (YFBM as % of original egg weight) | 43.84 ± 1.33$^a$ | 54.93 ± 3.99$^b$ |
| Yolk-sac (g) | 14.34 ± 0.90$^a$ | 14.59 ± 2.05$^a$ |
| %Yolk-sac (as % of original egg weight) | 23.99 ± 1.49$^a$ | 24.41 ± 2.90$^a$ |
| Tarsal length (cm) | 2.37 ± 0.17 | 3.12 ± 0.08$^b$ |
| Tibial length (cm) | 2.60 ± 0.04$^a$ | 2.98 ± 0.04$^b$ |
| Third digit length (cm) | 1.90 ± 0.07 | 2.20 ± 0.03$^b$ |

Hatchability

As seen from Table 3, in ovo application of probiotics was associated with a significant (P<0.05) increase in hatchability when compared to the control.

TABLE 3

Percent Hatchability of layer embryos with and without probiotic treatments

| Treatment Group | Hatchability |
| --- | --- |
| IO | 75.6% |
| Control | 68.1% |

Probiotic cocktail of *Lactobacillus paracasei* DUP-13076 and *L. rhamnosus* NRRL-B-442

Feed Conversion Ratio

In ovo and in-feed supplementation of probiotics led to a significant improvement in-feed Conversion Ratio (FCR) when compared to the control group. As can be seen from Table 4, throughout the grow-out period (week 1-5), supplementation of probiotics led to a significant improvement in FCR when compared to the untreated control. With the IO group (in ovo supplementation only, no in-feed supplementation), provision of probiotics only during the embryonic phase can be seen to translate into better performance in the grow-out birds even in the absence of sustained probiotic supplementation. This highlights the importance of promoting embryonic growth to enhance overall production and performance in chicken. However, birds in the IOIF group that received sustained probiotic supplementation (in ovo and in-feed) performed significantly (P<0.05) better than IO and EC birds.

TABLE 4

Feed conversion ratio (Pullets) of different treatment groups

| Week | EC | IO | IOIF |
| --- | --- | --- | --- |
| 1 | 2.590737$^a$ | 2.242295$^b$ | 2.236764$^b$ |
| 3 | 3.621683$^d$ | 3.427331$^e$ | 3.32564$^e$ |
| 4 | 5.432861$^g$ | 4.689375$^h$ | 4.359595$^i$ |
| 5 | 5.332861$^j$ | 4.889375$^k$ | 4.459595$^l$ |

$^{a-l}$different superscripts indicate a significant difference in mean.

Body Weight and Organ Weights

Figure 2:
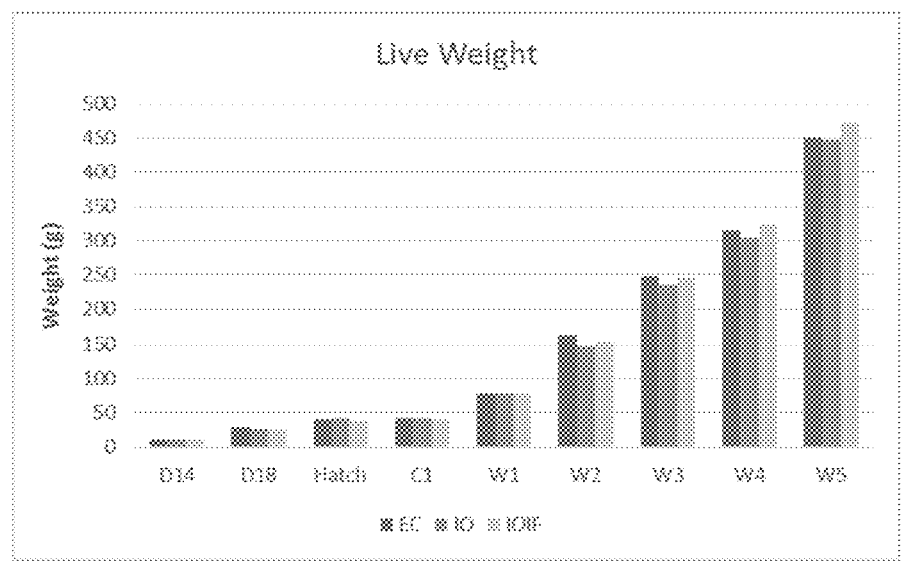
FIG. 2 is a bar graph showing mean live weight in layer embryos, hatchlings and pullets.

Body Weight:

Treatment groups supplemented with probiotics were seen to have a higher body weight throughout the experiment when compared to the control (FIG. 2; Table 5).

TABLE 5

Effect of probiotic supplementation on embryo and chick weight (g) in layers.

| | Treatment groups | |
| --- | --- | --- |
| Days/Week | Control | Probiotic treatment (IOIF) |
| D14 | 10.48 ± 0.51$^a$ | 11.73 ± 0.33$^b$ |
| D18 | 25.48 ± 0.52$^a$ | 27.44 ± 0.31$^b$ |
| D21 | 38.92 ± 0.57$^a$ | 41.64 ± 0.51$^b$ |
| W1 | 74.61 ± 1.55$^a$ | 78.85 ± 1.59$^b$ |
| W3 | 239.97 ± 5.33a | 259.84 ± 4.91b |

Body Length and Bone Lengths

Figure 3:
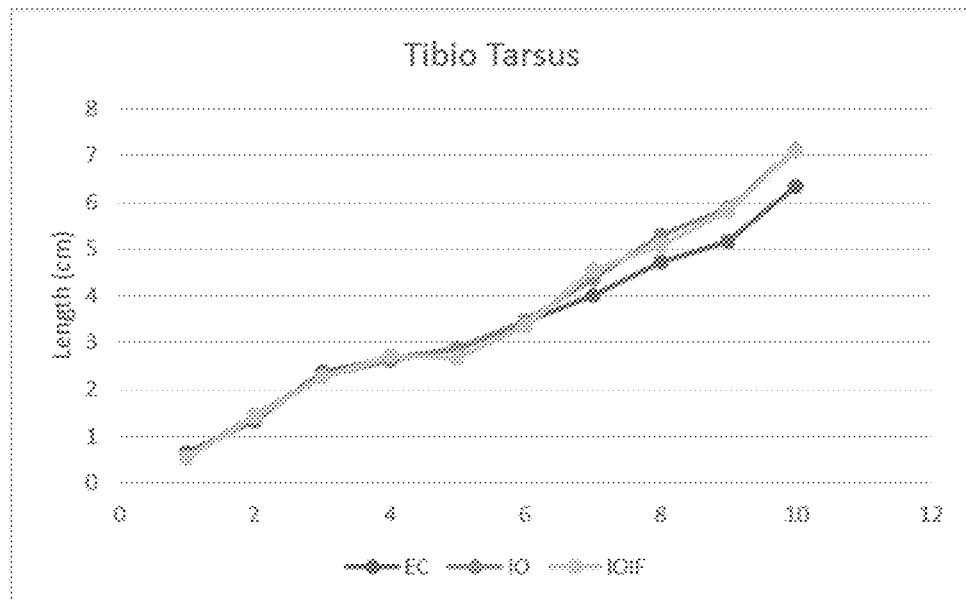
FIG. 3 is a line graph showing tibio tarsus length in layers versus time.
Figure 4:
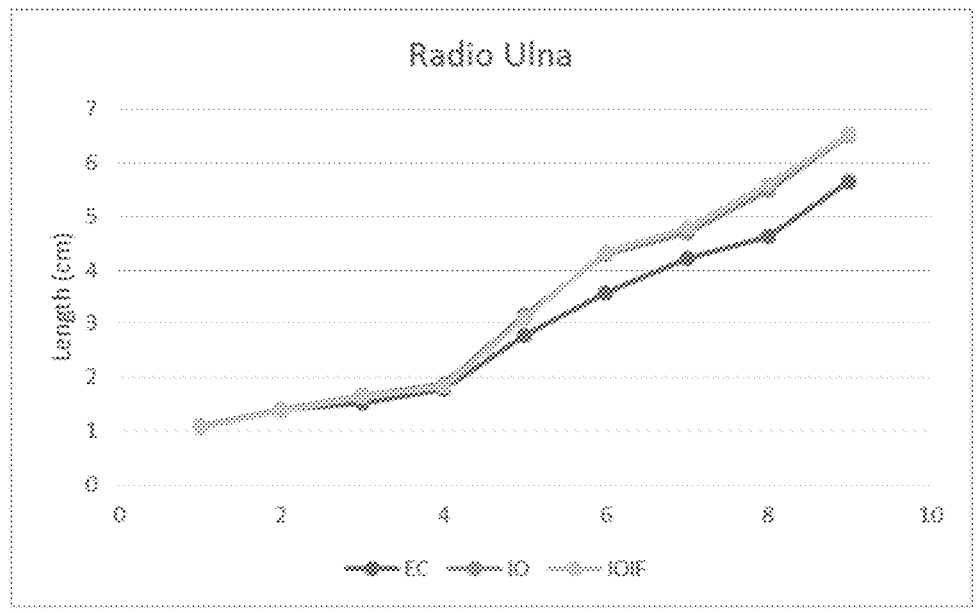
FIG. 4 is a line graph showing radio ulna length in layers versus time.

Treatment groups that received probiotics during their embryonic growth and development tended to be taller (crown-rump length; FIG. 1) and have longer bones compared to chickens with no probiotic exposure (FIG. 3-4). Both tibio-tarsus and radio-ulna lengths were significantly longer in IO and IOIF compared to EC, which indicates that probiotic application during embryonic growth and development has stimulated bone growth post-hatch (FIGS. 3 and 4).

Conclusion

Results of the study demonstrate that improving embryonic growth can significantly improve post-hatch, growth and performance as seen from the improved FCR and increase in other growth parameters including weight gain, RTC, breast weight and bone length. Additionally, in ovo probiotic application also improved hatchability when compared to the untreated eggs. Overall, sustained probiotic supplementation including in ovo and in-feed application was found to have an enhanced effect on growth and development when compared to in ovo supplementation alone.

Experimental Design

Broilers:

This study was carried out according to the guidelines of the University of Connecticut Institutional Animal Care and Use Committee. Freshly laid fertile Ross 308 eggs (Aviagen, Huntsville, Ala.) were collected and randomly assigned to the following 3 groups. The 3 treatment groups were: i) Control (PBS) ii) LP (or Lp): In ovo and in-feed *L. paracasei* DUP-13076 supplementation [Eggs will be sprayed with 200 µl (~9 log CFU/egg on days 1, 3, 7, 10, 14, and 18 of incubation) probiotic, followed by in-feed supplementation (~9 log CFU/kg of feed) until week 5, iii) LR (or Lr): In-ovo and in-feed *L. rhamnosus* NRRL-B-442 supplementation [Eggs will be sprayed with 200 µl (~9 log CFU/egg on days 1, 3, 7, 10, 14, and 18 of incubation) probiotic, followed by in-feed supplementation (~9 log CFU/kg of feed).

1. Egg Treatment, Incubation, and Sampling

Eggs in each group were weighed and sprayed with the probiotic treatment or PBS using an atomizer. The sprayed eggs were then incubated in a thermostat incubator (2362N *Hova*-Bator, GQF Manufacturing Company Inc., GA) with an automatic egg turner (1611 egg turner with 6 universal racks, GQF Manufacturing Company Inc.), temperature and humidity control for 18 days at 37.8° C. and 55% relative humidity. During this period, ten eggs per treatment were sampled on days 7, 10, 14 and 18.

2. Embryonic Parameters

Morphometric measurements including head, heart, liver, gizzard, breast, leg, yolk-free embryo mass and embryo weights, crown-rump length, tibio tarsal length and the length of the third digit were measured during the embryonic period.

3. Quantitative Colorimetric Assay for Glycogen

Muscle, liver, and yolk tissue samples from the $18^{th}$ day of incubation were thawed and homogenized in 25 mM citrate and 2.5 g/L sodium fluoride buffer (pH, 4.2) on ice. The samples were then centrifuged 14,000×g for 5 min, and 10 µL clear supernatant was used for the assay. The supernatants were tested for glycogen content using the Enzy-Chrom Glycogen Assay kit (BioAssay Systems, Hayward, Calif.) per manufacturer's instructions. Briefly, 10 µL of supernatant was added to individual wells in a 96-well flat-bottomed plate, followed by the addition of a single working reagent that enzymatically converts glycogen into glucose and detects glucose with a colorimetric assay read at 570 nm absorbance. For quantitative glycogen assessment, glycogen values were calculated from a standard curve run with a linear range from 50 to 200 µm/mL.

4. Hatchability and Post-Hatch Performance Parameters

On day 18, the remaining eggs were sprayed with probiotics or PBS and transferred to the hatcher and held at 37.8° C. and 65% relative humidity for 3 days or until hatch. On the day of hatch (day 21), percent hatchability was recorded, and hatchlings were weighed prior to placement on floor pens. Ten hatchlings from each treatment group were sacrificed, and morphometric measurements were performed as described above. Entire gizzard, liver, breast, and thigh were collected, weighed and expressed relative to body weight.

5. Chicken Diet and Management

A standard management procedure was used throughout the experiment. Day-old chicks were transferred to floor pens, and feed/water was administered ad libitum for the entire 5 week experimental period. All birds were grouped in separate pens depending on the treatment type. Birds of each group received feed supplementation similar to the treatment they obtained while they were embryos. The appropriate volume of the probiotic culture was added to the feed and mixed thoroughly to obtain the desired concentration (~9 log CFU/g) in the feed.

6. Body Weight and Feed Conversion Ratio

Prior to feeding, individual body weights were obtained on week 1, 3, and 5. Feed consumed was recorded daily on per pen basis, the uneaten feed was collected once daily before morning feeding and feed conversion ratio was calculated as the proportion of live weight over the feed consumed.

7. Organ Weights and Carcass Yield Percentages

On weeks 1, 3, and 5, ten birds from each treatment group were sacrificed. Internal organs, gizzard, heart, liver, breast, and thigh, were collected. Both absolute and relative organ weight were calculated. Head and feet of the bird were removed, followed by defeathering, and evisceration so that the carcass was in a ready to cook (RTC) state. RTC carcass weight was measured and expressed as a percentage of live body weight.

Results:

Supplementation of Probiotics During Early Phase of Embryonic Development (Day 0 of Egg Incubation) Enhances Embryonic Growth in Broiler Embryos:

Results from this study demonstrated that early probiotic supplementation significantly increased ($P \leq 0.05$) all tested parameters in the treatment groups when compared with the control (Table 6). Of interest is the significant increase in embryo weight (~5-7%) and crown rump length (8.1 cm vs 8.6 cm) in treatment groups compared to the control (Table 6). This is noteworthy since longer chicks have been associated with better use of egg nutrients and higher post hatch growth. In addition, there was no significant difference in the yolk-sac weight or its percentage relative to original egg weight between the different groups (Table 6). This suggests that the observed increase in embryo weight in the treatment groups (in the absence of a proportionate decrease in yolk sac mass) may be attributed to better nutrient utilization in the probiotic groups (LR and LP) as opposed to the control. Further, we did not observe any gross morphological changes in the internal organs. Additionally, probiotic supplementation did not exert any adverse effects on embryo viability.

TABLE 6

Biometric measurements of broiler embryos (d 18 of incubation) treated, with different probiotic strains

| Parameters | Treatment groups | | |
|---|---|---|---|
| | Control | LR | LP |
| Egg weight (g) | $65.34 \pm 1.14^a$ | $64.75 \pm 0.56^a$ | $64.01 \pm 1.19^a$ |
| Embryo weight (g) | $30.15 \pm 0.27^a$ | $32.43 \pm 0.43^b$ | $31.85 \pm 0.51^b$ |
| Embryo weight per egg weight (%) | $46.26 \pm 0.02^a$ | $50.14 \pm 0.01^b$ | $49.84 \pm 0.01^b$ |
| Embryo weight difference (%) | | +7.56 | +5.64 |
| Yolk-sac(g) | $19.70 \pm 0.93^a$ | $19.17 \pm 1.20^a$ | $19.73 \pm 0.1^a$ |
| Yolk-sac per egg weight (%) | $30.26 \pm 0.02^a$ | $29.57 \pm 0.02^a$ | $30.86 \pm 0.01^a$ |
| Crown rump length (cm) | $8.15 \pm 0.11^a$ | $8.62 \pm 0.08^b$ | $8.68 \pm 0.13^b$ |

Figure 5:
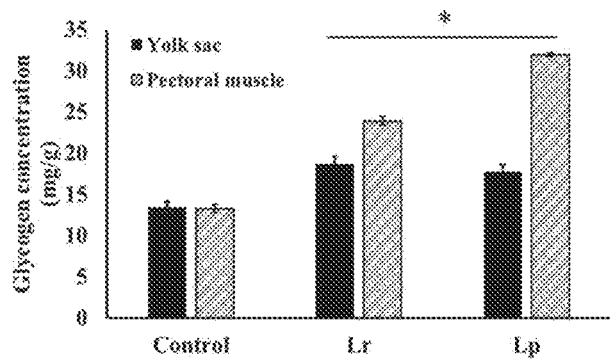
FIG. 5 is a bar graph showing glycogen content in the yok sac and pectoral muscle of broiler embryos on day 18 of incubation.

Probiotic Supplementation Improves Glycogen Reserves in the Yolk Sac of Late-Term Embryos:

Because probiotic treatment resulted in increased late-term embryonic growth we investigated the effect of probiotic supplementation on carbohydrate levels (glycogen) in the yolk sac. Briefly, yolk sac contents (membrane+contents; n=10/group) were sampled on day 18 and analyzed for their glycogen content. As seen from FIG. 5, probiotic treated embryos contained a significantly higher level of glycogen as compared to the control. This increased level of carbohydrate reserves may provide the energy and fuel necessary to promote late-term embryonic growth as observed in Table 6.

Probiotic Supplementation Improve Hatchability:

Hatchability is calculated as the percentage of eggs hatched to the number of fertile eggs during 19.5 and 21.5 days of incubation, and the results can be found in Table 7. The overall hatchability in the control was 73.3% and all of these eggs hatched in 19.5-20.5 days period, no additional eggs hatched for next 24 h. The hatchability in the LR group was 95%, where 83.3% hatched during 19.5-20.5 day period and the rest of the eggs (11.7%) hatched during 20.5-21.5 days period. Hatchability in LP (75%) group was similar to that of the control group.

TABLE 7

The effect of probiotic spray on hatchability of broiler eggs

|  | Control | B442 | B13076 |
| --- | --- | --- | --- |
| Total Hatchability (%) | 73.33 | 95.00 | 75.00 |
| within 19.5-20.5 days (%) | 73.33 | 83.30 | 61.60 |
| within 20.5-21.5 days (%) | 0.00 | 11.70 | 13.40 |

Probiotic Supplementation Improves Embryonic and Post-Hatch Growth in Broilers (Live Weight, FCR, Relative Breast Weight and Dressing Percentage)

Figure 6:
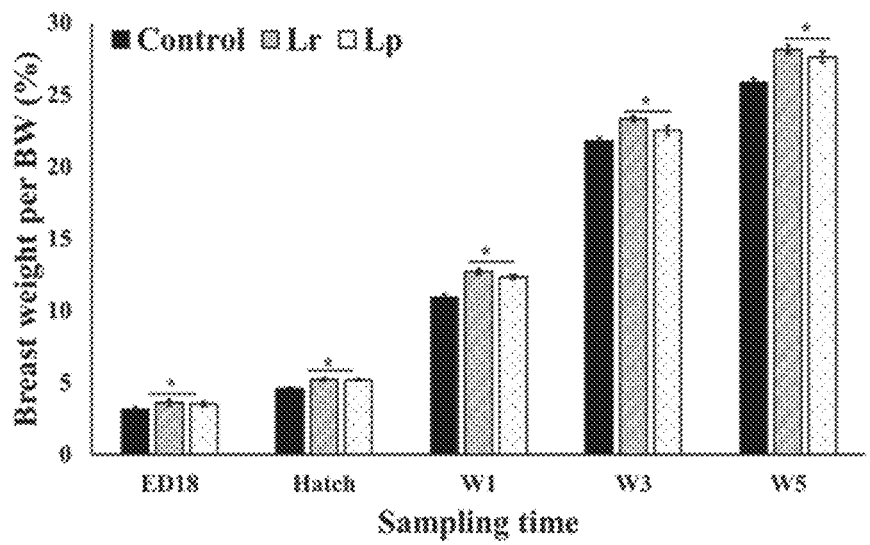
FIG. 6 is a bar graph showing the effect of administration of the probiotic compositions provided herein on relative breast weight in broilers.

As seen from Table 8, early probiotic supplementation not only improved embryonic development but also provided sustained enhancement of post-hatch growth in chicks. Although combined average weights are presented here, significant effect of sex was observed in all groups with male chicks being significantly larger than female birds in all treatment groups (P<0.05). Overall, early probiotic treatment resulted in higher body weights (Table 8) and relative breast weight (FIG. 6) throughout the study period. Additionally, a significant increase in carcass weight and dressing percentage was also observed in the probiotic treatment groups. For instance, on week 5 post-hatch, the dressing percentage in the probiotic groups was 68-70% when compared to 63% in the control group. Furthermore, this increase in growth was found to be associated with an improvement in-feed conversion efficiency in the probiotic treated groups (Table 8).

TABLE 8

Effect of probiotic supplementation on embryo, live weight and FCR (feed conversion ration) in broilers

| Days/Week | Control | Lr | Lp |
| --- | --- | --- | --- |
| ED18 | 29.68 ± 0.77$^a$ | 32.80 ± 0.72$^b$ | 31.48 ± 0.56$^b$ |
| Hatch* | 43.99 ± 1.07$^a$ | 46.82 ± 0.65$^b$ | 46.64 ± 0.75$^b$ |
| W1* | 147.95 ± 3.05$^a$ | 163.07 ± 3.16$^b$ | 159.44 ± 3.16$^b$ |
| W3* | 847.11 ± 25.11$^a$ | 930.75 ± 17.09$^b$ | 944.89 ± 17.40$^b$ |
| W5* | 1676.04 ± 49.32$^a$ | 1841 ± 65.71$^b$ | 1822.79 ± 59.13$^b$ |
| FCR at W5 | 1.65 | 1.51 | 1.64 |

Data are represented as average ± SEM;
*combined average for male and female chicks.
$^{a-b}$Means with different superscripts within a row are significantly different at P ≤ 0.05

Conclusion

Results of the study demonstrate that improving embryonic growth can significantly improve post-hatch, growth and performance as seen from the improved FCR and increase in other performance parameters including weight gain and relative breast weight. Additionally, in ovo probiotic application also improved hatchability when compared to the untreated eggs. Overall, sustained probiotic supplementation including in ovo and in-feed application was found to have an enhanced effect economically important traits in broilers.

Example 2: Effect of In Ovo and In-Feed Probiotic Supplementation on Embryonic Growth, Production Performance, Meat Quality and Cecal Microbiome in Broilers This study analyzes the effects of different live and heat-killed probiotics on improving embryonic growth parameters, hatchability, broiler production performance and feed efficiency.

Materials and Methods

LAB Culture Conditions and Preparation of Probiotic Spray

Probiotic strains, *L. paracasei* DUP-13076 (LP), and *L. rhamnosus* NRRL-B-442 (LR) were obtained from Dr. Bhunia, Food Science Department, Purdue University, and the USDA NRRL culture collection, respectively. Each strain was cultured separately in 10 ml of de Mann, Rogosa, Sharpe broth (MRS) under at 37° C. for 24 hours. The cells were then sedimented by centrifugation (3600×g for 15 min), washed twice with sterile phosphate buffered saline (PBS, pH 7.0), and resuspended in 10 ml PBS. Heat-inactivated cultures were prepared as described by Sashihara et al., *J. Dairy Sci.* 89, 2846-2855 (2006). Briefly, the cells harvested in a refrigerated centrifuge (10,000×g, 15 min) after overnight incubation and washed twice with PBS solution. The cells were then resuspended in sterile PBS; heat-killed at 75° C. for 60 minutes in a water bath. The commercial probiotic (Primalac, Star Labs Inc., Clarksdale, Mo.) was resuspended in PBS or added at 1 g/kg as per manufacturer's instructions, and it contained primarily *Lactobacillus acidophilus* and *Lactobacillus casei*.

Experimental Design

The study was carried out according to the guidelines of the University of Connecticut's Institutional Animal Care and Use Committee. Freshly laid fertile Ross 308 eggs (Aviagen, Huntsville, Ala., USA) were randomly assigned to the following 6 groups. A total of 840 eggs were used with 140 eggs per group. The 6 treatment groups were: i) Control (PBS): In ovo and in-feed [Eggs were be sprayed with PBS (200 µl/egg on days 1, 3, 7, 10, 14, and 18 of incubation) followed by in-feed supplementation 5 ml/kg of feed) until week 5] ii) LP: In ovo and in-feed *L. paracasei* DUP-13076 supplementation [Eggs were sprayed with 200 µl of LP (~9 log CFU/egg on days 1, 3, 7, 10, 14, and 18 of incubation), followed by in-feed supplementation (~9 log CFU/kg of feed) until week 5], iii) LR: In ovo and in-feed *L. rhamnosus* NRRL-B-442 supplementation (probiotic application similar to LP), iv) HI-LP: In ovo and in-feed heat-inactivated *L. paracasei* DUP-13076 supplementation (treatment application similar to LP), v) HI-LR: In ovo and in-feed heat-inactivated *L. rhamnosus* NRRL-B-442 supplementation (treatment application similar to LP) and vi) Primalac: In ovo and in-feed supplementation of Primalac (treatment application similar to LP).

Egg Treatment, Incubation, and Sampling

Eggs in each group were weighed and sprayed with the probiotic treatment or PBS using an atomizer. The sprayed eggs were then incubated in a thermostat incubator (2362N Hova-Bator, GQF Manufacturing Company Inc., GA) with an automatic egg turner (1611 egg turner with 6 universal racks, GQF Manufacturing Company Inc.), temperature and humidity control for 18 days at 37.8° C. and 55% relative humidity. During this period, ten eggs per treatment were sampled on days 7, 10, 14 and 18.

Embryonic Parameters

Morphometric measurements including head, heart, liver, gizzard, breast, leg, yolk-free embryo mass and embryo weights, crown-rump length, tibiotarsal length and the length of the third digit were measured during the embryonic period.

Quantitative Colorimetric Assay for Glycogen

Muscle, liver, and yolk tissue samples from the $18^{th}$ day of incubation were thawed and homogenized in 25 mM citrate and 2.5 g/L sodium fluoride buffer (pH, 4.2) on ice. The samples were then centrifuged 14,000×g for 5 min, and 10 μL clear supernatant was used for the assay. The supernatants were tested for glycogen content using the Enzy-Chrom Glycogen Assay kit (BioAssay Systems, Hayward, Calif.) per manufacturer's instructions. Briefly, 10 μl of supernatant was added to individual wells in a 96-well flat-bottomed plate, followed by the addition of a single working reagent that enzymatically converts glycogen into glucose and detects glucose with a colorimetric assay read at 570 nm absorbance. For quantitative glycogen assessment, glycogen values were calculated from a standard curve run with a linear range from 50 to 200 μm/mL.

Hatchability and Post-Hatch Performance Parameters

On day 18, the remaining eggs were sprayed with probiotics or PBS and transferred to the hatcher and held at 37.8° C. and 65% relative humidity for 3 days or until hatch. On the day of hatch (day 21), percent hatchability was recorded, and hatchlings were weighed prior to placement on floor pens. Ten hatchlings from each treatment group were sacrificed, and morphometric measurements were performed as described above. Entire gizzard, liver, breast, and thigh were collected, weighed and expressed relative to body weight.

Chicken Diet and Management

A standard management procedure was used throughout the experiment. Day-old chicks were sexed, transferred to floor pens, and feed/water was administered ad libitum for the entire 5 week experimental period. Birds were reared in a deep litter system with wood shavings as the litter material. The room temperature in the first week was 35° C. and was gradually reduced to decreased to 25° C. until the end of the experiment. Lighting system was automated, 22 h of light was provided in the first week and was later reduced to 20 h. Birds of each group received feed supplementation similar to the treatment they obtained while they were embryos. Appropriate dilutions of the probiotic culture were added to the feed and mixed thoroughly to obtain the desired concentration (~9 log CFU/g) in the feed. The chicks were fed with the starter diets (Crude protein—23%) from days 1 to 13 and grower feed (crude protein—18%) from day 14-42.

Body Weight and Feed Conversion Ratio

Prior to feeding, individual body weights were obtained on week 1, 3, and 5. Feed consumed was recorded daily on per pen basis, the uneaten feed was collected once daily before morning feeding and feed conversion ratio was calculated as the proportion of live weight over the feed consumed.

Organ Weights and Carcass Yield Percentages

On weeks 1, 3, and 5, ten birds from each treatment group were sacrificed. Internal organs, gizzard, heart, liver, breast, and thigh, were collected. Both absolute and relative organ weight were calculated. Head and feet of the bird were removed, followed by defeathering, and evisceration so that the carcass was in a ready to cook (RTC) state. RTC carcass weight was measured and expressed as a percentage of live body weight.

pH, Drip Loss and Meat Color

Breast muscle samples from market age birds (week 5) were analyzed for meat quality parameters including pH, drip loss and color. pH of the breast muscle (Pectoralis major) was measured at 2 and 24 h postmortem with a portable pH meter (Ross, ThermoFisher Scientific, MA, USA) by inserting a glass electrode directly in the thickest part of the muscle. The water-holding capacity of meat was estimated by measuring drip loss of the raw meat after storage: the pectoralis major muscle was weighed 2 h postmortem and immediately placed in a plastic bag and stored at 4° C. After 24 h, the sample was wiped with absorbent paper and weighed again. The difference in weight corresponded to the drip loss and was expressed as the percentage of the initial muscle weight. Breast meat color of 5-week old birds was measured at 2 h and 24 h following sacrifice on the upper ventral side of the *P. major* muscle using a Miniscan Spectrocolorimeter™. Color was measured by the CIELAB™ system, where L* represents lightness, a* redness, and b* yellowness. Higher L*, a*, and b* values correspond to paler, redder and more yellow meat, respectively.

Microbiome Analysis

For the microbiome analysis, cecal contents from the control, LP and LR groups were collected on week 1 and week 3 post-hatch. Following collection, the samples were stored at −80° C. until further processing. DNA extraction and QC analysis were performed at CGI as per standard protocols. Multiplex sequencing reactions were performed on an Illumina Mi-Seg™ platform with an average read length of 250 base pairs, and 16 S DNA paired-end library was created. Mothur v1.39.5™ was used for quality control, data trimming and making OTU clustering. Unique fasta sequences were aligned with custom Silva seed database, (Silva.seed.v_128.align) with starting length of 13862 and cutoff of 23444. The sequences that did not align to reference database were removed. The data were then preclustered to 1% to reduce the computational time, and the reads were then classified with reference to Silva.seed.v_128.tax with a cutoff of 80. OTU classification was done up to four taxa levels, and alpha and beta diversities were measured using Bray-Curtis, Jaccard, and theta-yc. A rarefied OTU table was made to create the heat map and select indicator species.

Statistical Analysis

The obtained data were analyzed according to general linear model (GLM) of SAS according to the following model: $Y_{ijk}=\mu+G_i+T_j+GT_{ij}+e_{ijk}$, where $Y_{ijk}$ is an observation, μ is the overall mean, $G_i$ is the effect of different treatment groups, $T_j$ is the effect of the sampling time, $IT_{ij}$ is the effect of interaction between the treatment group and time, and $e_{ij}$ is the random error. The significant differences between least squares means were tested at the level of P<0.05 using Duncan's multiple-range test (Duncan 1955). For microbiome analysis, non-metric multidimensional scaling (NMDS) using Bray-Curtis distance and diversity analyses (Inverse-Simpson) were performed on rarefied count data (sample size of 10,000 reads) using the phyloseq package in R. All correlations and tests with p<0.05 were considered significant. All analyses and graphics were generated in R version 3.15.0 (R project, Statistical Software): http://www.R-project.org.

Results and Discussion

Pre-Hatch

The effect of probiotic spray on embryo weight during incubation are presented in Table 9. The results indicate that there was no significant difference in mean embryo weight between treatment groups on days 7, 10, or 14. On the $18^{th}$ day of incubation, mean embryo weights of LR, HI-LR, and control (31.85 g, 32.71 g and 31.22 respectively) were significantly (p<0.05) different and higher than that of LP, HI-LP and Primalac (39.32 g, 28.88 g and 27.01 g respectively). On days 7, 10 and 14, the highest mean embryo weights were observed with LR (1.17 g, 3.01 g, and 13.95 g respectively on days 7, 10 and 14) and LP (1.19 g, 3.03 g and 13.36 g respectively on days 7, 10 and 14). Overall, LR and LP have higher mean embryo weights compared to other groups during incubation and embryos treated with heat-inactivated LR and LP have lower mean embryo weights compared to their live counterparts. On days 10, 14 and 18, Primalac treated embryos were the smallest (Table 9). The relative embryo weights were calculated as the percentage of embryo weight to the initial egg weight. The effect of probiotic spray on relative embryo weights on days 7, 10, 14 and 18 of incubation compared to the initial egg weights are shown in Table 9. There was no significant difference in relative embryo weight among different groups on day 7, 10 and 14. However, the highest mean relative values were obtained with LR and LP during these time points. The relative embryonic weights were significantly (p<0.05) higher in LR and HI-LR (50.17% and 49.51% respectively) compared to any other group on day 18 and the lowest relative weights were seen among Primalac and LP groups (43.47% and 45.05% respectively). The breast (1.08 g) and leg (1.5 g) weights of embryos were lowest in Primalac group on day 18 (p<0.05) as shown in Table 10. Highest mean breast weight was observed in LR (1.5 g) on day 18 and was significantly higher than HI-LR and Primalac (p<0.05). Similarly, highest mean leg weight was seen in LR (2.03 g) on day 18. Relative breast and leg weights were calculated as the percentage of breast and leg weights to the embryo weight and represented in Table 10. No significant difference in relative breast weight was observed between the treatment groups on day 18. However, the highest mean relative value was seen in the LR group (4.73%) and was lowest in Primalac (4.01%). The relative leg weight was lowest in Primalac (5.57%) and was significantly lower than the other groups.

The effect of probiotic spray on crown-rump lengths of embryos on days 7, 10, 14 and 18 of incubation is shown in Table 9. There was no significant difference in crown-rump lengths between different treatment groups on days 7, 10 and 14. However, LR, HI-LR, and control embryos were significantly (p<0.05) longer compared to other groups and the mean crown-rump lengths were 89.17 mm, 86.11 mm and 87.15 mm respectively. The length of the third digit on day 18 was highest (24.01 mm) in the LR group and was significantly higher than LP, HI-LR, Primalac and Control as shown in Table 10. The tibiotarsal length was highest in the LR group (32.88 mm, p<0.05) and lowest in Primalac (29.05 mm), and no significant difference was detected between other groups.

TABLE 9

The effect of probiotic spray on mean embryo weights, relative embryo weights and crown-rump lengths on days 7, 10, 14 and 18 of incubation

| Time | Group | Embryo Weight (g) | Relative Embryo Weight (%) | Crown-Rump Length (mm) |
|---|---|---|---|---|
| Day 7 | Ctrl | 0.73 ± 0.39 bc | 1.09 ± 0.66 b | |
| | B13076 | 1.19 ± 0.47 abc | 1.79 ± 0.79 ab | |
| | B442 | 1.17 ± 0.42 abc | 1.76 ± 0.70 ab | |
| | HI13076 | 0.67 ± 0.38 c | 1.13 ± 0.63 b | |
| | HI442 | 1.09 ± 0.39 abc | 1.67 ± 0.66 ab | |
| | Primalac | 0.76 ± 0.36 bc | 1.19 ± 0.60 b | |
| Day 10 | Ctrl | 2.96 ± 0.47 ab | 4.51 ± 0.79 ab | 37.85 ± 1.12 a |
| | B13076 | 3.03 ± 0.42 a | 4.87 ± 0.70 a | 38.99 ± 0.99 a |
| | B442 | 3.02 ± 0.42 a | 4.56 ± 0.70 ab | 40.44 ± 0.99 a |
| | HI13076 | 2.70 ± 0.39 ab | 4.38 ± 0.66 ab | 35.73 ± 0.94 a |
| | HI442 | 2.84 ± 0.42 ab | 4.31 ± 0.70 ab | 39.37 ± 0.99 a |
| | Primalac | 2.72 ± 0.36 ab | 4.47 ± 0.60 ab | 38.51 ± 0.86 a |
| Day 14 | Ctrl | 12.80 ± 0.51 a | 20.00 ± 0.85 a | 64.39 ± 1.21 a |
| | B13076 | 13.36 ± 0.44 a | 20.21 ± 0.74 a | 64.38 ± 1.05 a |
| | B442 | 13.95 ± 0.44 a | 22.42 ± 0.74 a | 61.93 ± 1.05 a |
| | HI13076 | 12.63 ± 0.38 a | 20.42 ± 0.63 a | 61.34 ± 0.99 a |
| | HI442 | 12.90 ± 0.42 a | 19.67 ± 0.70 a | 62.36 ± 0.99 a |
| | Primalac | 12.13 ± 0.42 a | 20.21 ± 0.70 a | 60.62 ± 0.99 a |
| Day 18 | Ctrl | 31.23 ± 0.42 ab | 47.31 ± 0.70 ab | 87.16 ± 0.99 a |
| | B13076 | 29.32 ± 0.44 bc | 45.05 ± 0.74 bc | 81.73 ± 1.05 bc |
| | B442 | 31.86 ± 0.44 a | 50.17 ± 0.74 a | 89.17 ± 1.05 a |
| | HI13076 | 28.89 ± 0.36 cd | 47.47 ± 0.70 ab | 77.81 ± 0.86 c |
| | HI442 | 32.72 ± 0.42 a | 49.51 ± 0.70 a | 86.11 ± 0.99 ab |
| | Primalac | 27.02 ± 0.36 d | 43.47 ± 0.60 c | 80.92 ± 0.86 c |

*a-h: Different letters indicates the significant difference between the treatment groups within each time point for each parameter (p < 0.05). Cell values are mean ± standard error for each group.

TABLE 10

The effect of probiotic spray on third digit length, tibio-tarsal length, breast weight, leg weight, relative breast weight and relative leg weight of embryos on $18^{th}$ day of incubation

| Group | Third Digit length (mm) | Tibiotarasl length (mm) | Breast Weight (g) | Leg Weight (g) | Relative Breast Weight (%) | Relative Leg Weight (%) |
|---|---|---|---|---|---|---|
| Ctrl | 21.52 ± 0.51 bc | 31.78 ± 0.60 ab | 1.43 ± 0.06 ab | 1.85 ± 0.07 a | 4.60 ± 0.22 a | 5.93 ± 0.21 ab |
| B13076 | 19.59 ± 0.54 cd | 30.05 ± 0.63 bc | 1.36 ± 0.06 ab | 2.01 ± 0.08 a | 4.64 ± 0.23 a | 6.81 ± 0.22 a |
| B442 | 24.01 ± 0.54 a | 32.88 ± 0.63 a | 1.51 ± 0.06 a | 2.03 ± 0.08 a | 4.73 ± 0.23 a | 6.38 ± 0.22 ab |
| HI13076 | 22.78 ± 0.44 ab | 31.88 ± 0.52 ab | 1.25 ± 0.05 bc | 1.84 ± 0.06 a | 4.39 ± 0.19 a | 6.40 ± 0.18 a |

TABLE 10-continued

The effect of probiotic spray on third digit length, tibio-tarsal length, breast weight, leg weight, relative breast weight and relative leg weight of embryos on 18$^{th}$ day of incubation

| Group | Third Digit length (mm) | Tibiotarasl length (mm) | Breast Weight (g) | Leg Weight (g) | Relative Breast Weight (%) | Relative Leg Weight (%) |
|---|---|---|---|---|---|---|
| HI442 | 18.82 ± 0.51 d | 32.52 ± 0.60 ab | 1.49 ± 0.06 a | 2.07 ± 0.07 a | 4.57 ± 0.22 a | 6.34 ± 0.21 ab |
| Primalac | 20.41 ± 0.44 cd | 29.06 ± 0.52c | 1.08 ± 0.05 c | 1.51 ± 0.06 a | 4.01 ± 0.19 a | 5.57 ± 0.18 b |

*a-d: Different letters indicates the significant difference between the treatment groups within each time point for each parameter (p < 0.05). Cell values are mean ± standard error for each group.

Figure 7A:
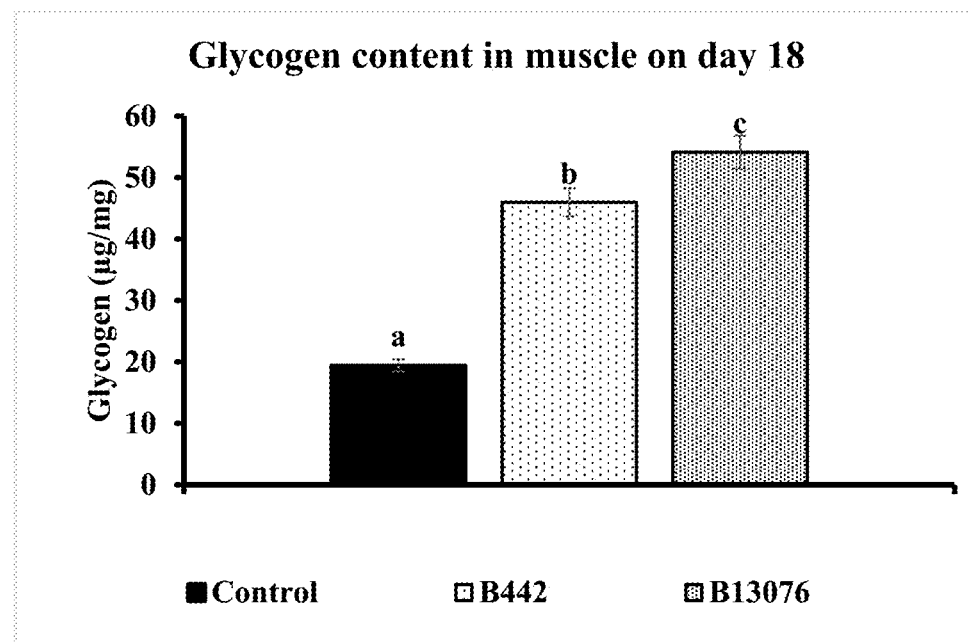
FIG. 7a is a bar graph showing the effect of administration of the probiotic spray composition described herein on glycogen content in pectoral muscle of broiler embryos on day 18.
Figure 7B:
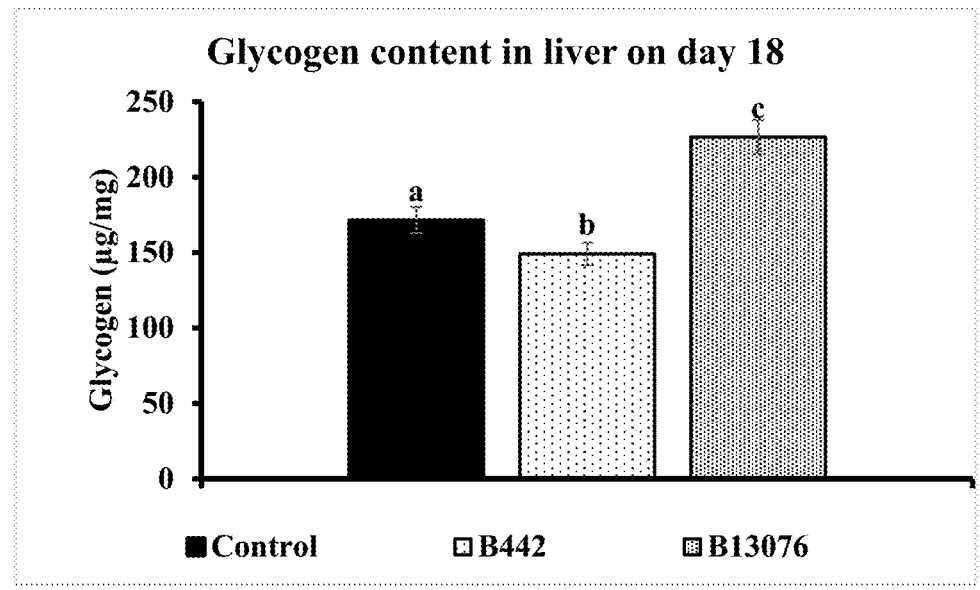
FIG. 7b is a bar graph showing the effect of administration of the probiotic spray composition described herein on glycogen content in liver of broiler embryos on day 18.
Figure 7C:
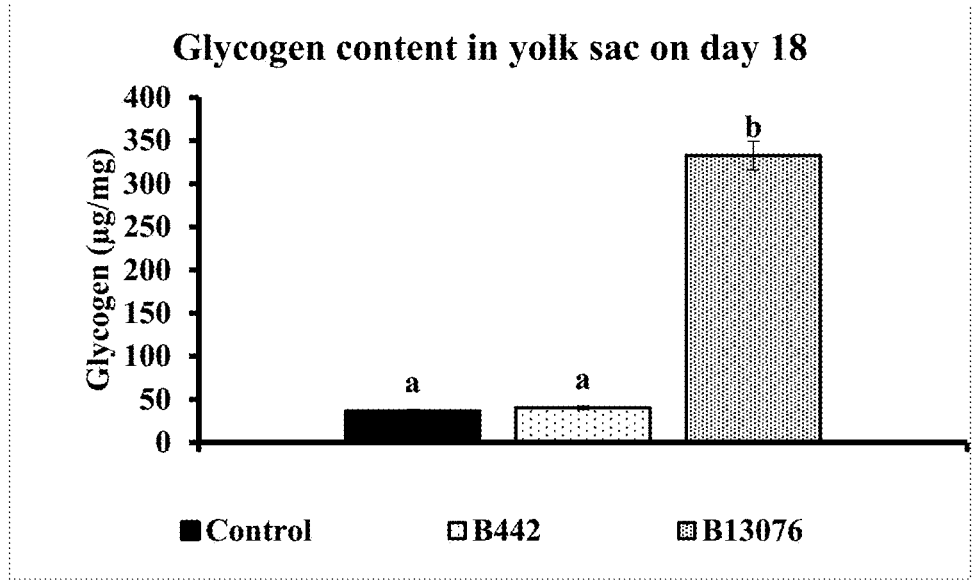
FIG. 7c is a bar graph showing the effect of administration of the probiotic spray composition provided herein on glycogen content in yolk sac of broiler embryos on day 18.

In addition to the morphometric parameters, glycogen content of muscle, liver and yolk sac were estimated on the 18$^{th}$ day of incubation to assess the energy status of the developing embryo. Since the heat-killed probiotics and Primalac were not found to perform as well the live probiotics, glycogen was estimated in samples collected from control, LP and LR. Glycogen concentration (μg/mg) of wet tissue in the pectoral muscle, liver and the yolk sac of late-term embryos (day 18) from control, LR and LP are shown in FIGS. 7 a-c. The glycogen content in muscle of control embryos was 20 μg/mg, while it was significantly higher in LR (45 μg/mg) and LP (55 μg/mg). In the liver, glycogen content of LR (150 μg/mg) was lower than the control (160 μg/mg) while liver samples from LP treated embryos had a significantly high glycogen content (227 μg/mg). There was no significant difference in glycogen content of yolk sac between control and LR (30 μg/mg), however, it was 325 μg/mg in LP. Several studies have demonstrated a positive correlation between the glycogen status level, hatchability and post-hatch performance. These studies suggest that depletion of glycogen reserves may occur due to the withdrawal of external food and lack of maternal nutrients. Uni et al., *Poult. Sci.* 84, 764-770 (2005), investigated the in ovo feeding of carbohydrates, and glycogen content was estimated in the muscle and liver. The results of this study demonstrated that in ovo carbohydrate feeding improved glycogen reserves in liver and muscle of perinatal embryos. This additional energy reserve supported the late-term embryo development resulting in significant increase in embryonic weight, relative embryo weight, mean breast weight and mean leg weight on day 18. Studies have demonstrated that hatchlings with enhanced glycogen reserve have higher body weight, reduced the mortality rate and enhanced performance.

Hatch

Hatchability is calculated as the percentage of eggs hatched to the number of fertile eggs set during 19.5 and 21.5 days of incubation, and the results are presented in Table 11.

TABLE 11

The effect of probiotic spray on hatchability of broiler embryos

|  | Control | B442 | B13076 | HI442 | HI13076 | Primalac |
|---|---|---|---|---|---|---|
| Total Hatchability (%) | 73.33 | 95.00 | 75.00 | 78.33 | 76.67 | 53.33 |
| within 19.5-20.5 days (%) | 73.33 | 83.30 | 61.60 | 78.33 | 76.67 | 42.20 |
| within 20.5-21.5 days (%) | 0.00 | 11.70 | 13.40 | 0.00 | 0.00 | 11.13 |

The overall hatchability in the control was 73.3% and all of these eggs hatched in 19.5-20.5 days period, no additional eggs hatched during the next 24 h. The hatchability in the LR group was 95%, where 83.3% hatched during 19.5-20.5 day period and the rest of the eggs (11.7%) hatched during 20.5-21.5 day period. Hatchability in LP (75%) group was similar to that of the control group. However, only 61.1% hatched during the first window and rest (13.4%) within the next 24 h. Similar to control, all the eggs in HI-LR (78.33%) and HI-LP (76.67%) hatched in the 19.5-20.5 day period. The highest mortality was observed in Primalac, where the hatchability was only 53.3% and only 42.2% of the eggs hatched in the first window. All the unhatched eggs were inspected, and it was noted that most of them were pipped from inside and mortality occurred towards the end of the incubation period. Different competitive exclusion products containing *Lactobacillus* have been administered to late-term embryos mainly to protect from pathogens once they hatch. These results indicate the hatchability depends on the bacterial strain, dose, and route of administration. This study suggests that early in ovo probiotic spray is an effective technique to improve the embryogenesis and hatchability of broilers.

The effect of in ovo probiotic spray on hatchling parameters are shown in Tables 12 and 13. The crown-rump length and tibiotarsal length of hatchlings were highest in the LR group (108.18±1.49 mm and 38.15±0.75 mm respectively). The crown-rump length and tibiotarsal length of LR was significantly (p<0.05) longer than the LP, HI-LP and Primalac, where the crown-rump lengths were 97.77±1.49 mm (LP), 94.98±1.49 mm (HI-LP) and 98.17±1.49 mm (Primalac), and the tibiotarsal length was 34.11±0.75 mm (LP), 37.19±0.75 (HI-LP) and 34.86±0.75 mm (Primalac), respectively (Table 12). Although the crown-rump and tibiotarsal were longer in LR, they were not significantly different than from the control and HI-LR. Molenaar et al., *Worlds Poult. Sci. J.* 64, 599-604 (2008), studied the correlation of hatchling length to later performance with two data set and observed a positive correlation between the hatchling length and slaughter weight in males, while, the same effect in females was observed only in one data set.

The effect of probiotic spray on mean live, RTC, breast, leg weights and relative RTC, breast and leg weights of chicks on the day of the hatch are shown in Table 12. Average body weight, ready to cook (RTC) weight and leg weight were significantly (p<0.05) lower in LP (live weight—45.56 g, RTC weight—16.44 g, leg weight—3.09 g), HI-LP (live weight—45.93 g, RTC weight—16.75 g, leg weight—3.21 g) and Primalac (live weight—44.61 g, RTC weight—16.3 g, leg weight—2.89 g). However, no significant difference was detected in mean breast weight, relative RTC weight, relative breast weight or relative leg weight.

Similarly, there was no significant difference in relative organ weights such as liver, heart, and gizzard among different treatment groups. O'Dea et al., *Poult. Sci.* 85, 1855-1863 (2006) sprayed commercial probiotics on chicken eggs and hatchling parameters were analyzed and did not find significant difference in hatchling weight between the control and treatment groups, however, the present study has improved hatchability with in ovo probiotic spray. Powell and Bowman have reported a positive correlation between hatchling weight and post-hatch performance in broilers (Powell and Bowman 1964). Nevertheless, different studies have reported contrasting results on correlation of hatchling weight with post-hatch performance.

TABLE 12

The effect of probiotic spray on crown-rump, third digit and tibiotarsal lengths of chicks on the day of hatch

| Group | Crown-Rump Length (mm) | Third Digit length (mm) | Tibiotarasl length (mm) |
|---|---|---|---|
| Ctrl | 102.91 ± 1.27 ab | 26.00 ± 0.35 ab | 37.20 ± 0.60 ab |
| B13076 | 97.77 ± 1.32 bc | 25.30 ± 0.77 ab | 34.11 ± 0.82 b |
| B442 | 108.18 ± 1.29 a | 25.88 ± 0.34 ab | 38.15 ± 0.64 a |
| HI13076 | 94.98 ± 2.10 c | 22.49 ± 2.17 b | 37.19 ± 0.83 b |
| HI442 | 103.78 ± 1.08 ab | 27.14 ± 0.47 a | 34.25 ± 0.88 ab |
| Primalac | 98.17 ± 1.12 be | 24.61 ± 0.39 ab | 34.86 ± 0.38 b |

*a-c: Different letters indicates the significant difference between the treatment groups within each time point for each parameter ($p < 0.05$). Cell values are mean ± standard error for each group.

TABLE 13

The effect of probiotic spray on mean live, RTC, breast, leg weights, and relative RTC, breast and leg weights of chicks on the day of hatch

| Group | Mean Live Weight (g) | RTC Weight (g) | Breast Weight (g) | Leg Weight (g) | Relative RTC Weight (%) | Relative Breast Weight (%) | Relative Leg Weight (%) |
|---|---|---|---|---|---|---|---|
| Ctrl | 52.31 ± 1.15 a | 19.06 ± 0.26 a | 1.65 ± 0.05 a | 3.61 ± 0.06 a | 36.51 ± 0.40 a | 3.16 ± 0.09 a | 6.91 ± 0.08 a |
| B13076 | 45.56 ± 0.86 cd | 16.44 ± 0.43 b | 1.48 ± 0.05 a | 3.09 ± 0.09 cd | 36.11 ± 0.70 a | 3.25 ± 0.10 a | 6.79 ± 0.21 a |
| B442 | 50.18 ± 1.27 ab | 18.50 ± 0.46 a | 1.72 ± 0.06 a | 3.56 ± 0.10 ab | 36.89 ± 0.36 a | 3.42 ± 0.10 a | 7.10 ± 0.12 a |
| HI13076 | 45.93 ± 1.33 bcd | 16.75 ± 0.43 b | 1.47 ± 0.06 a | 3.21 ± 0.08 bcd | 36.53 ± 0.45 a | 3.19 ± 0.11 a | 7.00 ± 0.15 a |
| HI442 | 49.57 ± 0.58 abc | 17.82 ± 0.28 ab | 1.52 ± 0.07 a | 3.27 ± 0.06 abc | 35.95 ± 0.42 a | 3.05 ± 0.14 a | 6.59 ± 0.13 a |
| Primalac | 44.61 ± 0.76 d | 16.30 ± 0.26 b | 1.57 ± 0.04 a | 2.89 ± 0.07 d | 36.58 ± 0.58 a | 3.53 ± 0.11 a | 6.47 ± 0.15 a |

*a-d: Different letters indicates the significant difference between the treatment groups within each time point for each parameter ($p < 0.05$). Cell values are mean ± standard error for each group.

Post-Hatch

Once the eggs hatched, probiotic supplementation was continued through feed until they were sacrificed. The effect of probiotic spray on eggshell surface and in-feed supplementation on crown-rump, third digit, and tibiotarsal lengths are presented in Table 14. There was no significant difference in crown-rump length, third digit and tibiotarsal lengths among different groups after seven days of growth. By the third week, third digit length (68 mm) and tibiotarsal length (94.85 mm) of HI-LP was significantly ($p<0.05$) longer than the other groups. However, the crown-rump length was longest in control (262.50±3.05 mm) but not significantly different than LR (258.40±2.49 mm) or Primalac (251.00±3.05 mm). By the time of slaughter, the crown-rump length of heat-inactivated probiotics was the smallest (HI-LR—282.5 mm, HI-LP—281.5 mm) and significantly different from other groups. Although LP had longest crown-rump and tibiotarsal by the fifth week, third digit length was longest in control. Increase in bone length measurement is an indication of growth rate. Mutus et al., *Poult. Sci.* 85, 1621-1625 (2006) investigated the effect of dietary probiotic supplementation on tibial bone characteristics and observed that probiotic supplementation did not affect the tibial length. However, the thickness of the medial and lateral wall of the tibia was significantly improved with probiotic supplementation.

TABLE 14

The effect of probiotic spray and in-feed supplementation on crown-rump, third digit and tibiotarsal lengths of chicks during growth period

| Time | Group | Crown-Rump Length (mm) | Third Digit length (mm) | Tibiotarasl length (mm) |
|---|---|---|---|---|
| Week 1 | Ctrl | 157.18 ± 2.03 a | 38.18 ± 0.69 a | 54.54 ± 0.54 a |
| | B13076 | 154.75 ± 2.60 a | 35.70 ± 0.87 a | 50.84 ± 1.58 b |
| | B442 | 154.64 ± 0.91 a | 37.54 ± 0.44 a | 56.07 ± 0.60 a |
| | HI13076 | 153.60 ± 1.49 a | 39.72 ± 0.72 b | 58.20 ± 0.99 c |
| | HI442 | 144.39 ± 4.04 a | 37.57 ± 0.36 a | 50.82 ± 0.75 b |
| | Primalac | 147.90 ± 4.44 a | 36.01 ± 1.07 a | 54.45 ± 1.42 a |
| Week 3 | Ctrl | 262.50 ± 3.05 a | 60.48 ± 1.20 b | 90.75 ± 1.66 b |
| | B13076 | 245.00 ± 3.05 be | 56.48 ± 1.20 b | 91.62 ± 1.66 b |
| | B442 | 258.40 ± 2.49 ab | 59.36 ± 0.98 b | 92.34 ± 1.36 b |
| | HI13076 | 235.70 ± 3.05 c | 68.00 ± 1.20 a | 94.85 ± 1.66 ab |
| | HI442 | 240.33 ± 2.64 c | 56.39 ± 0.92 b | 89.23 ± 1.36 b |
| | Primalac | 251.00 ± 3.05 abc | 56.46 ± 1.20 b | 90.10 ± 1.66 b |

TABLE 14-continued

The effect of probiotic spray and in-feed supplementation on crown-rump, third digit and tibiotarsal lengths of chicks during growth period

| Time | Group | Crown-Rump Length (mm) | Third Digit length (mm) | Tibiotarasl length (mm) |
|---|---|---|---|---|
| Week 5 | Ctrl | 305.00 ± 6.20 a | 75.00 ± 0.70 a | 109.00 ± 2.22 ab |
| | B13076 | 312.00 ± 5.79 b | 68.50 ± 1.70 b | 112.00 ± 2.25 a |
| | B442 | 302.50 ± 1.62 a | 73.20 ± 1.00 ab | 107.50 ± 2.85 ab |
| | HI13076 | 281.50 ± 2.65 c | 69.20 ± 1.44 ab | 111.26 ± 2.14 a |
| | HI442 | 282.50 ± 1.27 c | 69.93 ± 1.60 ab | 101.67 ± 1.96 be |
| | Primalac | 304.20 ± 2.6 a | 69.75 ± 1.23 ab | 111.33 ± 1.56 a |

*a-f Different letters indicates the significant difference between the treatment groups within each time point for each parameter ($p < 0.05$). Cell values are mean ± standard error for each group.

This study did not observe any significant difference in mean live weight, RTC weight and leg weight on weeks 1, 3 and 5. Similarly, mean breast weight was not significantly different on week 1 and 3. However, the mean breast weight of LP (456.09 g) and HI-LP (465.96 g) were significantly lower than other groups on slaughter (Table 15).

improved with probiotic supplementation. In the present study, besides carcass traits, relative heart, liver and gizzard weights were analyzed. Although no significant difference in heart and gizzard weight were observed, the relative liver weight of LR was observed to be higher (3.5%) on slaughter compared to the control (3.1%).

TABLE 15

The effect of probiotic spray and in-feed supplementation on mean live, RTC, breast and leg weights during growth period

| Time | Group | Mean Live Weight (g) | RTC Weight (g) | Breast Weight (g) | Leg Weight (g) |
|---|---|---|---|---|---|
| Week 1 | Ctrl | 202.54 ± 29.50 a | 96.26 ± 20.77 a | 24.50 ± 8.89 d | 16.04 ± 4.51 a |
| | B13076 | 179.31 ± 29.50 a | 83.57 ± 20.77 a | 21.92 ± 8.89 d | 13.43 ± 4.51 a |
| | B442 | 197.27 ± 28.13 a | 93.22 ± 19.81 a | 24.58 ± 8.47 d | 15.44 ± 4.30 a |
| | HI13076 | 209.60 ± 32.99 a | 104.57 ± 23.23 a | 29.12 ± 9.94 d | 16.29 ± 5.04 a |
| | HI442 | 186.02 ± 29.50 a | 86.89 ± 20.77 a | 21.45 ± 8.89 d | 14.22 ± 4.51 a |
| | Primalac | 182.58 ± 32.99 a | 88.38 ± 23.23 a | 26.58 ± 9.94 d | 13.50 ± 5.04 a |
| Week 3 | Ctrl | 1026.19 ± 29.50 a | 622.18 ± 20.77 a | 235.50 ± 8.89 a | 93.64 ± 4.51 a |
| | B13076 | 967.57 ± 29.50 a | 579.67 ± 20.77 a | 209.19 ± 8.89 a | 87.28 ± 4.51 a |
| | B442 | 977.80 ± 24.09 a | 594.54 ± 16.96 a | 222.74 ± 7.26 a | 89.82 ± 3.68 a |
| | HI13076 | 955.42 ± 29.50 a | 577.09 ± 20.77 a | 215.29 ± 8.89 a | 86.30 ± 4.51 a |
| | HI442 | 959.65 ± 24.09 a | 594.19 ± 16.96 a | 210.58 ± 7.26 a | 88.42 ± 3.68 a |
| | Primalac | 935.97 ± 29.50 a | 563.62 ± 20.77 a | 215.50 ± 8.89 a | 86.32 ± 4.51 a |
| Week 5 | Ctrl | 1805.41 ± 60.01 a | 1181.47 ± 44.11 a | 486.20 ± 17.95 ab | 151.74 ± 15.27 a |
| | B13076 | 1714.94 ± 57.87 a | 1109.34 ± 25.25 a | 456.09 ± 13.25 b | 161.90 ± 3.94 a |
| | B442 | 1736.90 ± 36.17 a | 1149.93 ± 39.54 a | 470.67 ± 15.82 ab | 171.92 ± 7.74 a |
| | HI13076 | 1734.50 ± 36.43 a | 1119.34 ± 39.29 a | 465.96 ± 12.66 b | 156.64 ± 4.99 a |
| | HI442 | 1754.48 ± 47.41 a | 1129.64 ± 35.05 a | 477.61 ± 12.61 ab | 167.63 ± 4.59 a |
| | Primalac | 1801.50 ± 52.44 a | 1161.55 ± 30.03 a | 512.85 ± 20.67 a | 167.35 ± 6.48 a |

*a-d Different letters indicates the significant difference between the treatment groups within each time point for each parameter ($p < 0.05$). Cell values are mean ± standard error for each group.

Relative RTC, breast and leg weights were calculated as the percentage of live weight on week 1, 3 and 5, and are shown in Table 16. No significant difference was observed in relative breast weight on week 3, relative leg weights on week 1 and 3, and relative RTC on week 3 among the different groups. Relative RTC weight was highest in LR (66.19%) and was significantly ($p<0.05$) higher than all other groups except control (65.36%). Relative RTC weight (46.57%), relative breast weight (12.21%) and relative leg weight (7.48%) were significantly lower ($p<0.05$) in the Primalac group. Although not significant LR and HI-LR had the highest relative breast weights, which are 27.12% and 27.21% respectively compared to control (26.93%). Similarly, the relative leg weight was significantly higher in the LR group (9.87%) compared to the control (8.49%). The relative RTC and leg weights of LR and LP were higher than their heat-killed counterparts (Table 16). Dilworth et al., *Poultry Science* 57, 1101 (1978) used *Lactobacillus* cultures as a feed additive in broilers and observed an improvement in growth rate. The growth of chicken was similar to the control when the suboptimal amino acid composition of the feed was the compounding factor. In contrast, Watkins and Kratzer, *Poult. Sci.* 63, 1671-1673 (1984) did not observe any effect on growth or feed conversion efficiency when *Lactobacillus* cultures were supplemented to broiler through drinking water. Pelicano et al., *Revista Brasileira de Ciencia Avicola* 5, 207-214 (2003) investigated the effect of dietary feed supplementation on broiler performance and did not find any significant difference in carcass yield or breast muscle yield. However, the leg yield was significantly

TABLE 16

The effect of probiotic spray and in-feed supplementation on Relative RTC, breast and leg weights during growth period

| Time | Group | Relative RTC Weight (%; Dressing percentage) | Relative Breast Weight (%) | Relative Leg Weight (%) |
|---|---|---|---|---|
| Week 1 | Ctrl | 47.52 ± 0.72 ab | 12.11 ± 0.43 bc | 7.92 ± 0.23 a |
| | B13076 | 46.57 ± 0.72 b | 12.21 ± 0.43 bc | 7.48 ± 0.23 a |
| | B442 | 47.20 ± 0.69 ab | 12.44 ± 0.41 b | 7.83 ± 0.22 a |
| | HI13076 | 49.86 ± 0.81 a | 13.88 ± 0.49 ab | 7.77 ± 0.26 a |
| | HI442 | 46.69 ± 0.72 b | 11.53 ± 0.43 c | 7.64 ± 0.23 a |
| | Primalac | 47.67 ± 0.81 ab | 14.07 ± 0.49 a | 7.23 ± 0.26 a |
| Week 3 | Ctrl | 60.59 ± 0.72 b | 22.98 ± 0.43 ab | 9.11 ± 0.23 a |
| | B13076 | 59.89 ± 0.72 b | 21.65 ± 0.43 c | 9.01 ± 0.23 a |
| | B442 | 60.83 ± 0.59 b | 22.83 ± 0.35 ab | 9.18 ± 0.19 a |
| | HI13076 | 60.41 ± 0.72 b | 22.55 ± 0.43 ab | 9.03 ± 0.23 a |
| | HI442 | 62.20 ± 0.59 a | 22.02 ± 0.35 bc | 9.25 ± 0.19 a |
| | Primalac | 60.27 ± 0.72 b | 23.02 ± 0.43 a | 9.24 ± 0.23 a |
| Week 5 | Ctrl | 65.36 ± 0.41 ab | 26.93 ± 0.38 a | 8.49 ± 0.08 b |
| | B13076 | 64.68 ± 0.40 b | 26.59 ± 0.47 a | 9.44 ± 0.08 ab |
| | B442 | 66.19 ± 0.31 a | 27.12 ± 0.38 a | 9.87 ± 0.21 a |
| | HI13076 | 64.47 ± 0.62 b | 26.90 ± 0.28 a | 9.03 ± 0.05 b |
| | HI442 | 64.28 ± 0.10 b | 27.21 ± 0.39 a | 9.55 ± 0.16 ab |
| | Primalac | 46.57 ± 0.22 c | 12.21 ± 0.01 b | 7.48 ± 0.17 c |

*a-d Different letters indicates the significant difference between the treatment groups within each time point for each parameter ($p < 0.05$). Cell values are mean ± standard error for each group.

The overall feed conversion efficiency is represented in Table 17. LR group was the most efficient in-feed conversion, which has a feed conversion ratio of 1.51 compared to the control which has 1.65. The FCR of Primalac group was comparable to that of LR and was 1.53. While LP has similar FCR to that of control, which is 1.64. HI-LP and HI-LR were less efficient that live probiotics and control and their FCR were 1.74 and 1.68 respectively. Studies have reported that in-feed probiotic supplementation can improve the FCR. While others have not noticed any difference in FCR between treated and untreated broilers. However results of this demonstrate that in ovo probiotic spray along with in-feed supplementation improved dressing percentage, relative leg weight, and feed conversion efficiency. The commercial probiotic, Primalac has been used previously to improve growth and performance. In the present study, although Primalac supplementation was associated with an improved FCR, the hatchability, growth parameters, dressing percentage, relative breast weight and relative leg weight were found to be the lowest among all groups tested. Overall, LR significantly improved the hatchability, growth, feed efficiency and slaughter weights.

TABLE 17

The effect of probiotic spray and in-feed supplementation on feed conversion ratio and meat quality (meat pH, drip loss of breast muscle) in broilers at slaughter

| Group | pH at 2 h | pH at 24 h | Change in pH | Drip loss (g) | FCR |
|---|---|---|---|---|---|
| Ctrl | 4.7967 ± 0.045 a | 4.8500 ± 0.018 a | 0.05333 ± 0.033 a | 4.7550 ± 1.4 a | 1.65 |
| B13076 | 4.6600 ± 0.017 a | 4.7383 ± 0.024 a | 0.07833 ± 0.017 a | 5.7917 ± 0.64 a | 1.64 |
| B442 | 4.7367 ± 0.025 a | 4.8250 ± 0.01 a | 0.08833 ± 0.024 a | 3.5183 ± 1.41 a | 1.51 |
| HI13076 | 4.7017 ± 0.017 a | 5.8500 ± 0.07 b | 1.1483 ± 0.065 b | 5.5500 ± 1.03 a | 1.74 |
| HI442 | 4.7150 ± 0.009 a | 4.7460 ± 0.008 a | 0.02800 ± 0.013 a | 4.1280 ± 1.29 a | 1.68 |
| Primalac | 4.8283 ± 0.125 a | 6.6700 ± 0.162 c | 1.8417 ± 0.24 b | 4.7667 ± 0.52 a | 1.53 |

*a-c Different letters indicates the significant difference between the treatment groups within the column (p < 0.05). Cell values are mean ± standard error for each group except for FCR.

Further, to evaluate the effect of probiotic supplementation on meat quality, luminosity, pH, meat color and drip loss were analyzed. The mean luminosity level was 49.4 in the control 2 h after slaughter which reduced to 45.64 after 24 h (Table 18). The meat from the LP group was less pale at 2 h (45.71), and paleness increased to 48.4 after 24 h. All other groups were paler than the control group at both time points. The probiotic treatments also significantly reduced the redness and yellowness of the meat compared to the control. The lightness values are comparable to the normal range (45-50), and the redness and yellowness were higher than the standard values (~4.5 for both yellowness and redness) in all the group including control. The pH was ~4.6-4.8 2 h after the slaughter in all the groups. The effect of probiotic treatment on pH and drip loss are shown in Table 17. After 24 h, the pH increased to around 4.7-4.8 in all groups except Primalac, which was 6.67. The pH values of meat in our study including the control group were lower than the reported normal values which are ~5.6-5.9, postmortem. The difference in stunning and bleeding procedure can affect the meat quality and pH. In our study, birds were euthanized using carbon dioxide and were not bled. Carbon dioxide stunning can result in a more rapid decrease in meat pH and better carcass quality compared to the electric stunning. Hence the variation in pH and meat color observed in this study could be due to the difference in processing technique we adopted. Drip loss was calculated as the difference in muscle weight at 2 h and 24 h postmortem. The lowest drip loss was observed with LR (3.5 g) compared to the control (4.8 g), LP (5.8 g), HI-LP (5.6 g), HI-LR (4.1 g) and Primalac (4.8 g) as shown in Table 17. This water loss can result in loss of nutrients and can make the meat less tender with loss of flavor. As seen the in Table 17, meat from LR treated birds had lowest drip loss, hence could prevent nutrient loss and may be able to preserve the flavor.

TABLE 18

The effect of probiotic spray and in-feed supplementation on pectoralis major color

| Group | L* | | | a* | | | b* | | |
|---|---|---|---|---|---|---|---|---|---|
| | 2 h | 24 h | ΔL* | 2 h | 24 h | Δa* | 2 h | 24 h | Δb* |
| Ctrl | 49.40 ± 0.04 a | 45.64 ± 0.01 a | 3.76 ± 4.7 a | 19.06 ± 0.088 a | 18.21 ± 4.45 ab | 0.85 ± 2.48 a | 21.92 ± 0.75 a | 19.19 ± 2.22 a | 2.74 ± 1.36 a |
| B13076 | 45.71 ± 0.17 b | 48.40 ± 0.02 b | −2.69 ± 1.16 b | 18.25 ± 1.34 a | 17.67 ± 0.97 a | 0.59 ± 1.11 a | 15.42 ± 0.61 b | 16.50 ± 1.18 a | −1.07 ± 1.1 a |
| B442 | 54.16 ± 0.02 c | 52.59 ± 0.01 c | 1.58 ± 1.05 ab | 15.51 ± 0.86 b | 17.51 ± 0.94 ab | −2.00 ± 0.48 a | 17.94 ± 0.68 c | 18.41 ± 0.6 a | −0.46 ± 1.47 a |
| HI13076 | 50.69 ± 0.01 d | 51.03 ± 0.07 d | −0.34 ± 0.63 ab | 16.52 ± 1.04 ab | 20.11 ± 0.98 b | −3.60 ± 1.4 a | 20.87 ± 0.55 d | 24.61 ± 0.96 b | −3.74 ± 1.47 b |
| HI442 | 54.41 ± 0.009 d | 55.10 ± 0.008 e | −0.22 ± 0.82 ab | 16.15 ± 0.88 ab | 18.37 ± 1.51 ab | −3.37 ± 1.4 a | 18.48 ± 1.1 c | 19.24 ± 1.39 ac | −1.47 ± 1.97 a |
| Primalac | 51.14 ± 0.12 e | 51.31 ± 0.16 f | −0.17 ± 1.23 ab | 14.91 ± 1.2 b | 18.05 ± 1.03 ab | −3.14 ± 1.07 a | 17.86 ± 0.74 c | 20.44 ± 0.93 c | −2.57 ± 0.89 a |

*a-f: Different letters indicates the significant difference between the treatment groups within the column (p < 0.05). Cell values are mean ± standard error for each group.

Figure 8:
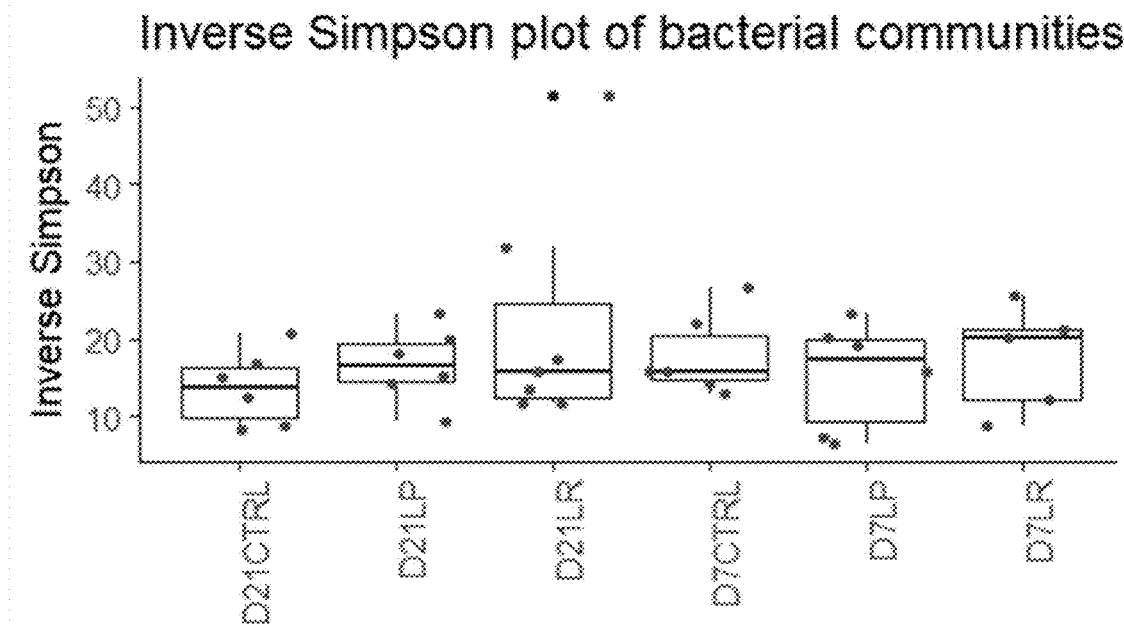
FIG. 8 is an inverse Simpson plot of cecal bacterial communities of different treatments groups on day 7 and 21 post-hatch in broiler chicks.
Figure 9:
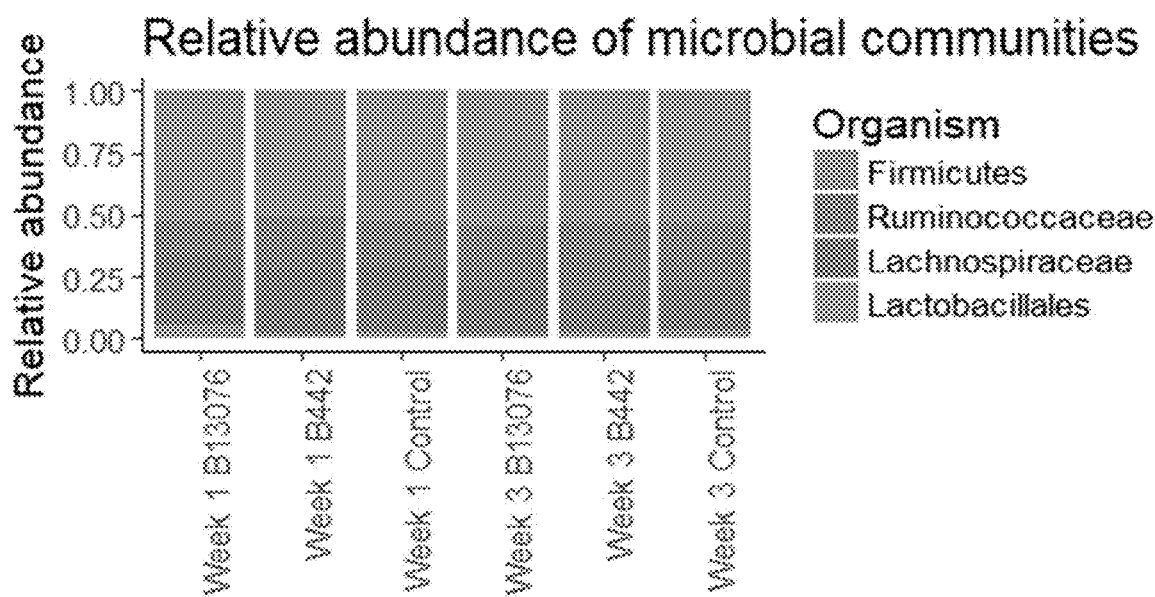
FIG. 9 is a bar graph showing relative abundance of cecal bacterial community versus abundance in broiler chicks on week 1 (day 7) and week 3 (day 21).

The colonization of the gut in animals occurs mostly during birth from the vaginal tract and from breastfeeding after birth. The colonized microbiome in animals not only influences the growth and development of the individuals, but also protects the infant from infection. Unlike mammals, natural microbiome colonization in birds occurs in the nest while the hen incubates the eggs. Since modern poultry management practices impede contact of the eggs with the hen during incubation, the major source of microbes to hatchling is the barn and hatchery environment. Moreover, artificial incubation delays the gastrointestinal tract colonization with microbes due to the lack of contact with adult birds. Even though enteric colonization in poultry mainly occurs after hatch; recent research demonstrates the presence of live microbes in the intestine of growing embryos. Therefore early probiotic supplementation could serve as potential means to modulate the microbiome in broiler chicks. The inverse Simpson plot was used to investigate the microbial diversity (FIG. 8). The median microbial richness index of LR and LP were higher than the control on day 7. By the third week, the richness index was highest for LR, followed by LP. The microbial community richness index indicates that in ovo probiotic administration followed by in-feed supplementation resulted in an increase in richness index over time (FIG. 9). A rarefied sample of 10000 OTUs was selected to create the heat map. The heatmap shows that both Firmicutes and Clostridiales were abundant in all the samples including control (FIG. 9). The relative abundance (FIG. 9) shows that Firmicutes were highest in LR on the day of hatch, and no difference was observed among other groups or time points. Ruminococcaceae and Lachnospiraceae were the major families found. In probiotic treated hatchlings, Ruminococcaceae was abundant than Lachnospiraceae in contrast to control. By week one, Lachnospiraceae became more abundant than Ruminococcaceae in all the groups. In contrast, Ruminococcaceae become more abundant than Lachnospiraceae by week 3 in all the groups. Ruminococcaceae were relatively more abundant in probiotic-treated groups on week 3 compared to the control. These results demonstrate that early and sustained application of probiotics could serve as an effective strategy to modulate the establishment and maintenance of the cecal microbiome in broiler chicks.

In conclusion, early in ovo probiotic supplementation improved the growth and development of chicken embryo which subsequently translated into later post-hatch performance. *L. rhamnosus* NRRL-B-442 was found to be most effective in improving embryonic growth parameters, hatchability, broiler production performance, feed efficiency and meat quality. Further, it was observed that live probiotics performed better than their heat-killed counterparts. The commercial probiotic, Primalac had significant negative effects on embryonic growth, hatchability and post-hatch performance. Overall, *L. rhamnosus* NRRL-B-442 could potentially be used as a safe and effective growth stimulant on embryonated eggs and in the feed to enhance the production performance in broilers.

Example 3: Early and Sustained Administration of Probiotics Promotes Embryo and Chick Growth in Layers This study investigated the use of probiotics to promote embryonic growth and post-hatch development in layer chicks.

Materials and Methods

LAB Culture Conditions and Preparation of Probiotic Spray

Probiotic strains, *L. paracasei* DUP-13076, and *L. rhamnosus* NRRL-B-442 were obtained from Dr. Bhunia, Food Science Department, Purdue University, and the USDA NRRL culture collection, respectively. Each strain was cultured separately in 10 ml of de Mann, Rogosa, Sharpe broth (MRS) at 37° C. for 24 h. The cells were then sedimented by centrifugation (3600×g for 15 min), washed twice with sterile phosphate buffered saline (PBS, pH 7.0), and resuspended in 10 ml PBS. The approximate bacterial count in each culture was determined spectrophotometrically. Equal portions from each of the strains were combined to make a two-strain probiotic cocktail. The bacterial population in the two-strain mixture was determined by plating 0.1-ml portions of appropriate dilutions on MRS agar, followed by incubation at 37° C. for 24 h. Appropriate dilutions of the two-strain mixture in PBS were used to obtain the desired level of inoculum (9 log CFU).

Experimental Design

Figure 10:
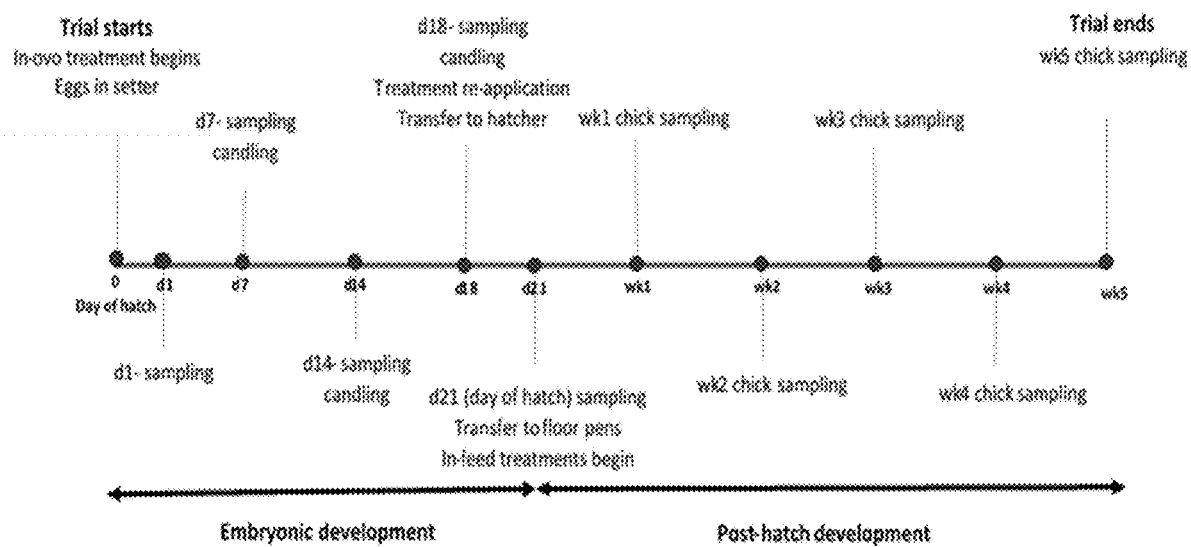
FIG. 10 is a schematic view of a time line showing the experimental design and sampling scheme utilized in the experiment.

Freshly laid fertile Lohmann LSL White Leghorn eggs were collected from the University of Connecticut poultry farm and randomly assigned to the following 4 groups. A total of 400 eggs were used with 70 eggs per group. The 4 treatment groups were: i) Egg control (EC; PBS only), ii) In ovo probiotic cocktail treatment (TO) on eggs (in ovo only; eggs were sprayed with 200 µl (~9 log CFU/egg) probiotic cocktail on days 1, 3, 7, 10, 14, and 18 of incubation), iii) In-feed probiotic supplementation (in-feed only; no egg treatment, only in-feed supplementation; ~9 log CFU/kg of feed) following hatch until sacrifice (IF) and iv) In ovo+ in-feed probiotic cocktail supplementation [Eggs will be sprayed with 200 µl (~9 log CFU/egg) probiotic, followed by in-feed supplementation (~9 log CFU/kg of feed) following hatch until sacrifice (IOIF)]. Experimental groups are summarized in Table 18, and experimental design and sampling scheme are shown in FIG. 10.

TABLE 19

| Treatment groups | | |
|---|---|---|
| Treatment groups (Pre-hath) | Treatment groups (Post-hatch) | Description |
| Control | EC | No treatment applied |
| | IF | Probiotic cocktail applied in-feed only |
| Probiotic | IO | Probiotic cocktail applied in ovo only |
| | IOIF | Probiotic cocktail applied both in-feed and in ovo |

Egg Treatment, Incubation, and Sampling

Eggs were weighed and kept at room temperature overnight. Eggs in group 2 (JO) and 4 (IOIF) were sprayed with 200 µl of the probiotic cocktail (~9 log CFU/egg) while eggs in group 1 (EC) and 3 (IF) were sprayed with PBS (solvent control; 200 µl of PBS/egg) using an atomizer. The sprayed eggs were then incubated in a thermostat incubator (2362N *Hova*-Bator, GQF Manufacturing Company Inc., GA) with an automatic egg turner (1611 egg turner with 6 universal racks, GQF Manufacturing Company Inc.), temperature and humidity control for 18 days at 37.8° C. and 55% relative humidity. During this period, ten eggs per treatment were sampled on days 1, 7, 14 and 18. These eggs were weighed, dipped in 50 ml PBS, rubbed for one minute, and the surviving probiotic population was enumerated by plating on MRS agar.

Morphometry of Embryos

In addition to probiotic enumeration, morphometric measurements including egg weight, heart, liver, breast, leg, yolk sac, yolk-free embryo mass and embryo weights, crown-rump length, tarsal length, tibial length and the length of the third digit were measured during the embryonic period.

Hatchability and Post-Hatch Performance Parameters

On day 18, the remaining eggs were sprayed with probiotics or PBS and transferred to the hatcher and held at 37.8° C. and 65% relative humidity for 3 days or until hatch. On the day of hatch (day 21), percent hatchability was recorded, and hatchlings were weighed prior to placement on floor pens. Ten hatchlings from each treatment group were sacrificed, and morphometric measurements were performed as described above. Blood was collected in non-heparinized vials to obtain serum for serum lipid analysis. Entire liver, breast, and thigh were collected, weighed and expressed relative to body weight.

Chicken Diet, and Management

Day-old chicks were sexed, transferred to floor pens, and feed/water was administered ad libitum for the entire 5 week experimental period. All birds were grouped in separate pens depending on the treatment type. The chicks were fed with the starter diets (Crude protein—18%; Calcium—0.9%). Birds were reared in deep litter system with wood shavings as litter materials. The room temperature in the first week was 35° C. and was gradually reduced to decreased to 25° C. until the end of experiment. Lighting system was automated, 22 h of light was provided in the first week and was later reduced to 20 h. Birds of each group received feed supplementation similar to the treatment they obtained while they were embryos (Table 19). For the in-feed supplementation, the probiotic cocktail was prepared as described previously. The appropriate volume of the cocktail culture was added to the feed and mixed thoroughly to obtain the desired concentration (~9 log CFU/g) in the feed.

Body Weight and Feed Conversion Ratio

Prior to feeding, individual body weights were obtained on week 1, 2, 3, 4 and 5. Feed consumed was recorded daily on per pen basis, the uneaten feed was collected once daily before morning feeding and feed conversion ratio was calculated as the proportion of live weight over the feed consumed.

Organ Weights

On weeks 1, 2, 3, 4 and 5, ten birds from each treatment group were sacrificed. At each sampling time, liver, breast, thigh, radio ulnar and tibia were collected. Both absolute and relative organ weight were calculated. Additionally, bone length, weight and diameter were also measured as an indicator of bone growth.

Serum Lipid Analysis

Blood samples collected at necropsy were centrifuged at 2000 g for 10 min, and the serum was transferred to vials and stored at −20° until lipid analysis. Serum samples were analyzed for total cholesterol, LDL and HDL cholesterol and triglycerides by colorimetric assay using EnzyChrom™ AF Cholesterol Assay and EnzyChrom™ Triglyceride Assay Kits (BioAssay Systems, CA).

Statistical Analysis

A completely randomized design with factorial treatment structure was followed. For the first part of the experiment involving the eggs, the experimental unit was a hovabator that received different treated-diets (100 eggs per incubator), and the sampling unit was the egg. For the morphometric measurements, the factors include 4 treatments (control, TO, IF, IOIF), 6 parameters (organ and embryo weight, crown-rump length, tarsal length, tibial length and the length of the third digit), and 4 time points (day 1, 7, 14 and 18). For the second part of the study involving hatchling/chicken, the experimental unit was the pen of chickens that received different diets (60 birds/pen), and the sampling unit was the bird. In the chicken performance data, the factors included the 4 treatments, 4 parameters (body weight, carcass weight, feed intake, feed conversion rate), and 5 time points (week 1, 2, 3, 4 and 5). In organ weight data, the factors included 4 treatments, 5 samples (gizzard, heart, liver, breast and thigh), and 5 time points (week 1, 2, 3, 4 and 5). The proc-MIXED and proc-PLM procedures of the SAS (SAS Institute Inc. Cary, N.C.) were used for the analysis. When appropriate, means comparisons were made using the least square means and differences between least square means were separated. The significance was considered at $p<0.05$. Further, the data were analyzed using a multi-level growth model to analyze the effect of probiotics on pullet growth. The model used was $Y=M+time+Group+Gender_m+e$, where M is the estimate; time is different sampling point from week 3 through 5; the group is different treatment groups, such as IO, IF, IOIF; gender is male; and e is the error. The values of female birds on the second week was considered as the base value.

Results and Discussion

This study investigated the effect of in ovo and in-feed probiotic supplementation to improve embryo and pullet growth in layers.

Embryo and Hatchling

Figure 11:
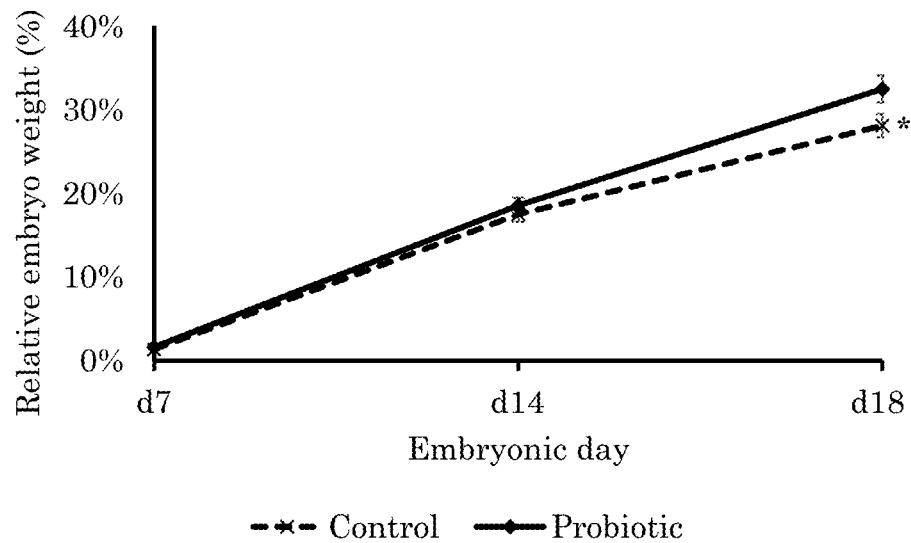
FIG. 11 is a line graph of relative embryo weight versus embryonic day showing relative body weight of layer embryos during incubation.
Figure 12:
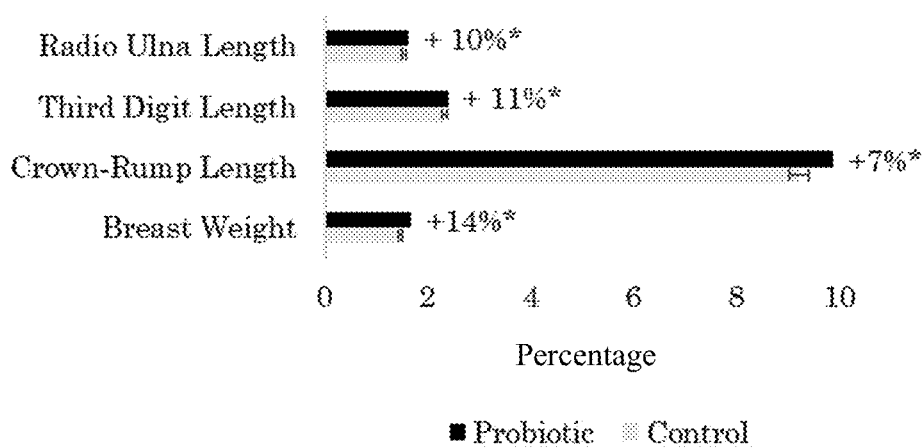
FIG. 12 is a bar graph showing morphometric measurements (relative measures) of layer embryos during incubation.

On $7^{th}$, $14^{th}$ and $18^{th}$ day of incubation, relative embryo weights were significantly higher ($p<0.05$) in the probiotic group (16.05%, 18.55%, and 32.5%) compared to the control group (13.32%, 17.49%, and 28.11%; FIG. 11). With the other parameters including crown-rump length, radioulnar length and length of the third digit (FIGS. 12 and 13), significant difference was observed between the control and probiotic group ($p<0.05$). In addition, there was no significant difference in the yolk-sac weight or its percentage relative to the original egg weight between the different groups. This suggests that the observed increase in embryo weight in the treatment groups (in the absence of a proportionate decrease in yolk sac mass) may be attributed to better nutrient utilization in the probiotic group as opposed to the control. Further, we did not observe any gross morphological changes in the internal organs. Following 18 days of incubation, the eggs were transferred to the hatcher and monitored for hatch. Spray application of probiotics on to layer embryos led to a significant increase in hatchability ($p<0.05$). Hatchability of the probiotic-treated group was 78.5% compared to the control which was 75.55%.

Figure 13:
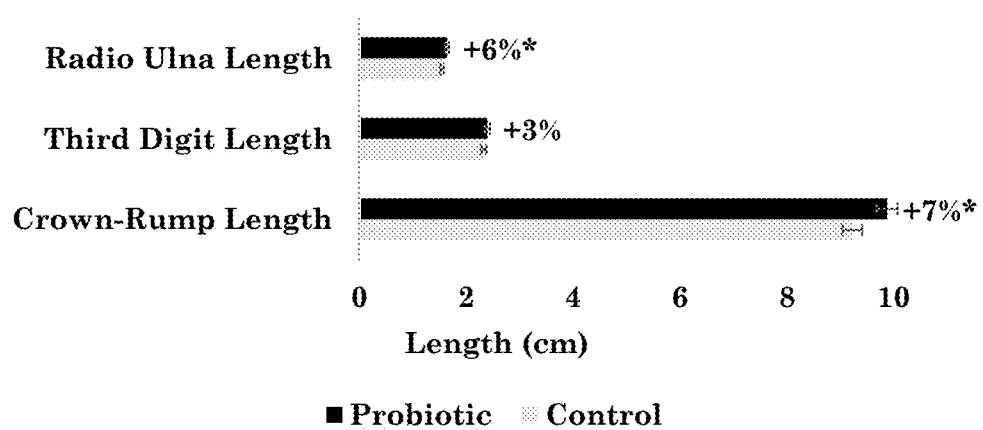
FIG. 13 is a bar graph showing length measurements of layer chicks on day of hatch.
Figure 15:
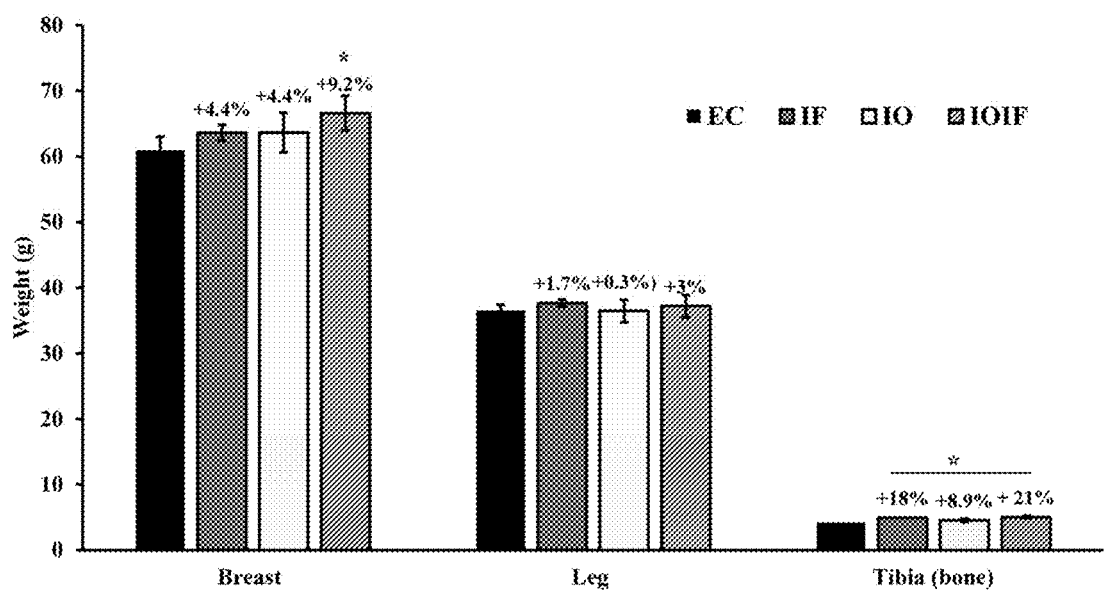
FIG. 15 is a bar graph showing breast, leg and bone weights of pullets at week 5 post-hatch.

On the day of the hatch, the live weight of the hatchling did not differ ($p>0.05$) between the control group (39.775±0.54 g) and the probiotic-treated group (40.2±0.53 g). Further, absolute breast, leg, and liver weights were significantly higher in the probiotic group compared to the control group. The absolute breast, leg, and liver weights were increased by 14%, 7%, and 11% respectively, as shown in FIG. 15. In accordance with the absolute weights, relative weights of breast, leg, and liver were also higher ($p<0.05$) in the probiotic group. Also, in ovo probiotic application increased crown-rump length by 7%, radio-ulna length by 6% and third digit by 3% when compared to the control (FIG. 13). Similar studies performed by Pender et al., *Beneficial microbes* 7, 699-705 (2016) did not observe any significant difference in hatchability following in ovo inoculation of probiotics via the air sac. To the contrary, in the present study significant increase in hatchability and hatchling morphometry was observed. The difference in the observed results could be attributed to the probiotic application as early as day one of incubation, difference in the method of application (route) and strain of bacteria. Overall, chicks hatched from probiotic sprayed eggs were longer and heavier than the control. This is noteworthy since longer chicks have been associated with better use of egg nutrients and higher post-hatch growth. As opposed to the crown-rump length, body weight has a low predictive value on post-hatch performance. In this study chicks in a probiotic group on the day of hatch were 7% longer (p<0.05), while they were 1% heavier (p>0.05) than the control group.

Post-Hatch

Figure 14:
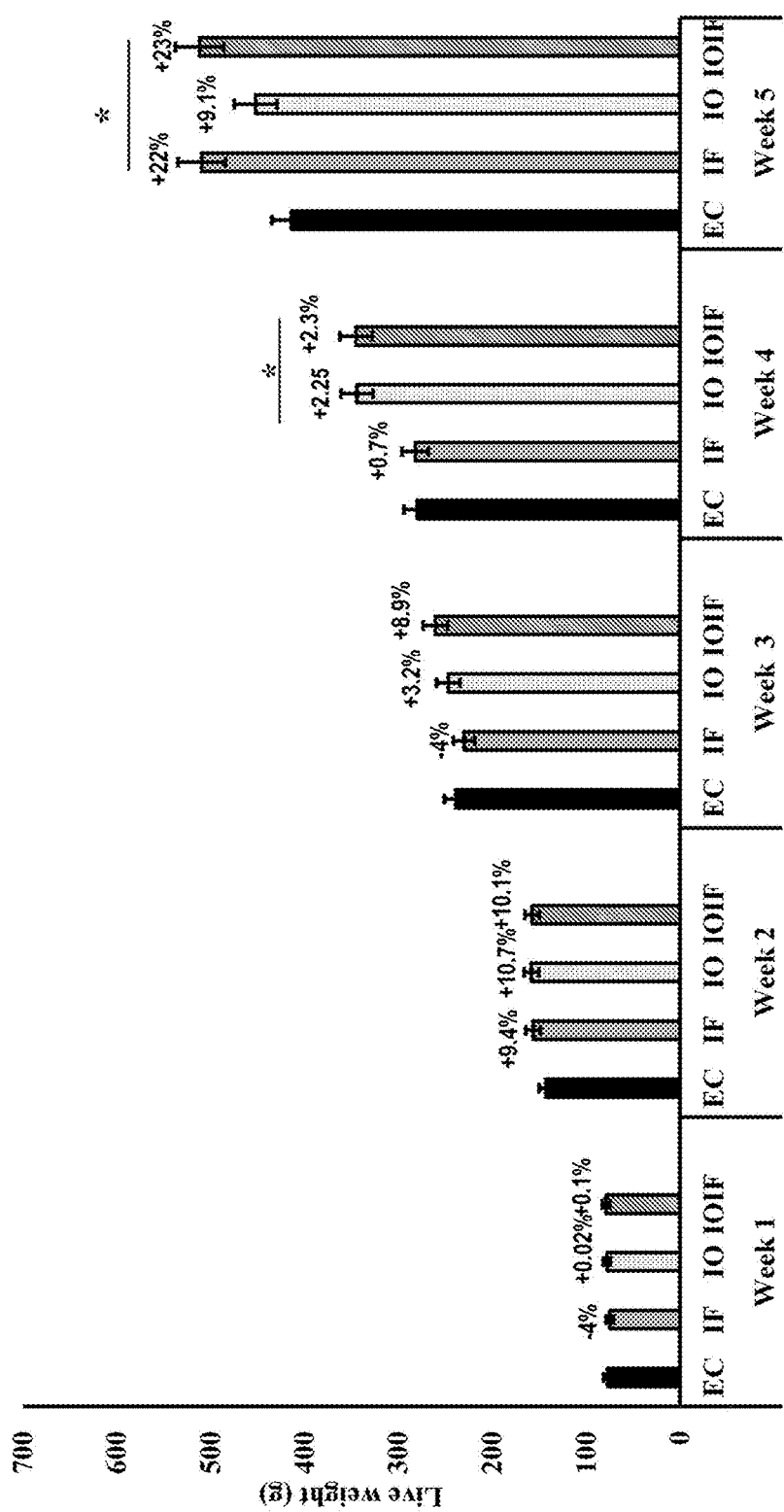
FIG. 14 is a bar graph showing the effect of administration of the probiotic composition described herein on pullet live weight over time.

As seen in FIG. 14 during the post-hatch period, supplementation with probiotics was associated with higher live weights when compared to the control. For instance, the mean live weight of the chicks by $5^{th}$ week was higher (p<0.05) in the IOIF (511.84±17.22 g) and IF (509.43±18.79 the length measurements, which indicates that in ovo probiotic spray is the reason for increased body lengths of chicks.

Figure 21:
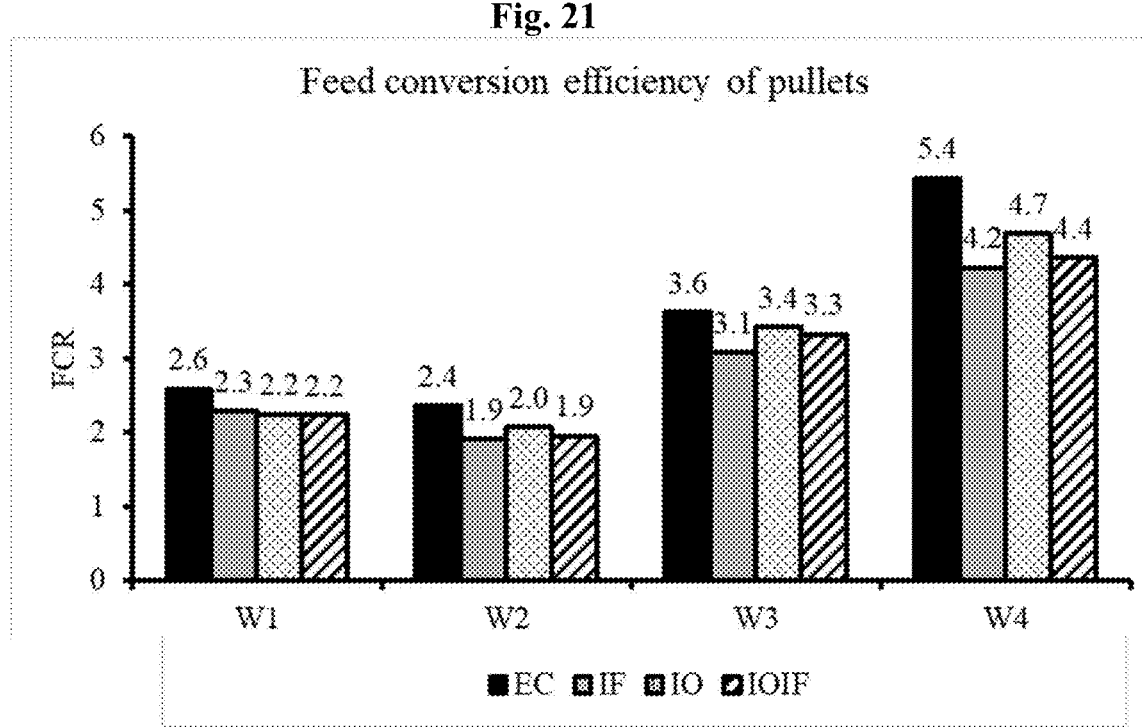
FIG. 21 is a bar graph showing feed conversion ratio of pullets in different treatment groups on week 5.

An important parameter to be considered in poultry production is feed conversion ratio or the efficiency of feed utilization by the birds. In the present study supplementation of probiotics was found to improve FCR (FIG. 21). It can be seen that FCR was significantly lower when probiotic treatment was applied either on egg surface or in-feed compared to the control group. The average FCR (week 5) was lowest in IF (3.17) and IOIF (3.27) followed by IO (3.46) and was highest in the EC (3.87). Therefore, both in ovo and in-feed probiotic supplementation have better feed efficiency than the control. Based on the model, overall male chicks were bigger than female birds. Further, IOIF was associated with the highest increase in all morphometric parameters measured over time (Table 20).

TABLE 20

Multilevel modeling of growth in pullets

| Parameter | Mean (g/cm) | + Week 3 (g/cm) | + Week 4 (g/cm) | + Week 5 (g/cm) | + IF (g/cm) | + IO (g/cm) | + IOIF (g/cm) | + Male (g/cm) | + error (g/cm) |
|---|---|---|---|---|---|---|---|---|---|
| Live weight | 209.75 | 106.87 | 148.43 | 257.61 | 5.80 | −6.23 | 8.13 | 33.06 | 28.48 |
| Breast weight | 27.08 | 13.03 | 19.63 | 39.58 | 0.79 | −1.82 | 2.41 | 5.39 | 4.40 |
| Leg weight | 16.32 | 7.89 | 11.79 | 21.57 | 0.38 | −0.67 | 1.10 | 2.22 | 2.65 |
| Liver weight | 8.72 | 2.76 | 4.39 | 6.56 | 0.36 | −0.37 | 0.34 | 1.02 | 1.37 |
| Crown rump length | 17.48 | 2.48 | 3.46 | 7.16 | −0.38 | 0.73 | 0.30 | 0.43 | 0.75 |
| Tibio tarsus length | 4.54 | 0.82 | 1.16 | 1.96 | −0.06 | 0.30 | 0.80 | 0.23 | 0.29 |
| Radio Ulna length | 4.00 | 0.70 | 1.02 | 2.0 | −0.11 | 0.60 | 0.73 | 0.10 | 0.21 | g) groups when compared with IO (452.21±21.9 g) and EC (414.47±20.1 g; FIG. 14). Similarly, breast weight increased in all the treatment groups compared to EC, IOIF increased breast weight by 9.2%, while with IF and IO, it was 4.4% (FIG. 15). The leg weight did not differ between the EC and IO. However, it was greater in IOIF and IF by 3% and 1.7% respectively compared to the control. The observed results in the present study demonstrate an increase in body weight following probiotic supplementation.

Figure 18:
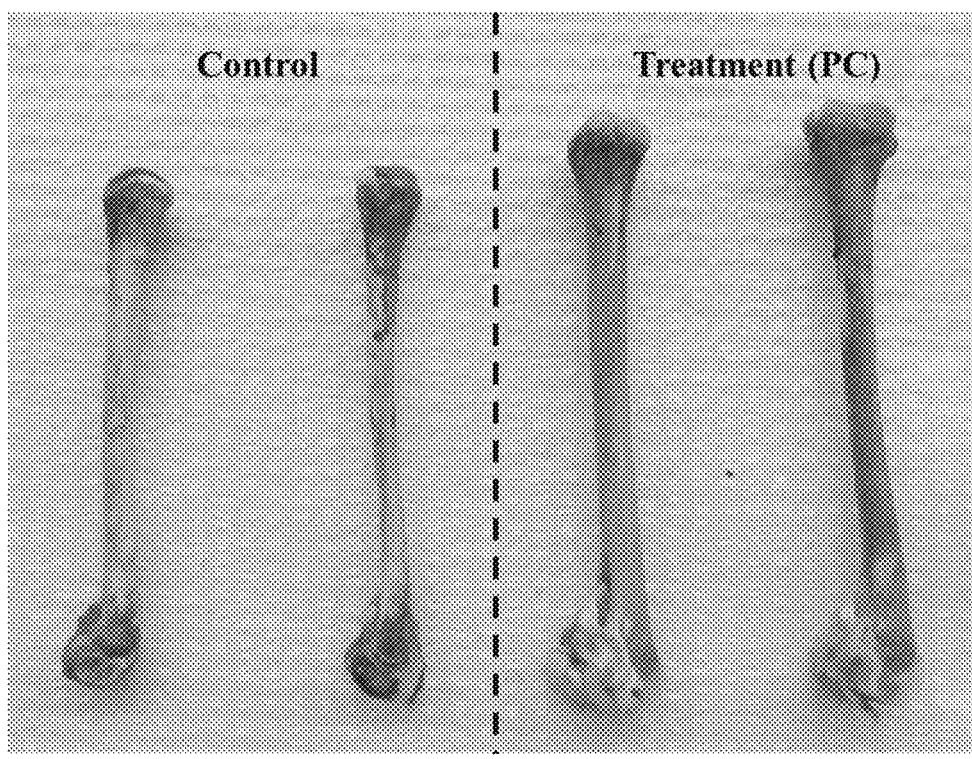
FIG. 18 is a photograph showing representative images of tibia from pullets at 5 weeks of age with and without (control) treatment.
Figure 19:
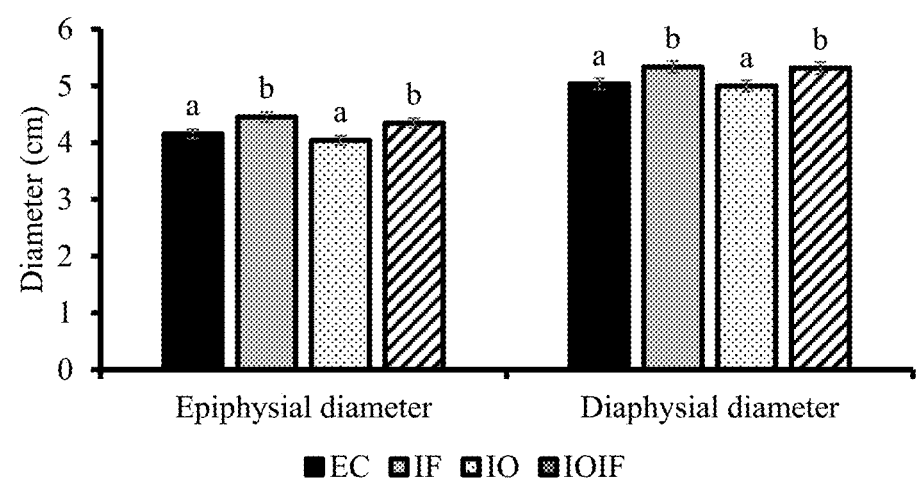
FIG. 19 is a bar graph showing epiphyseal and diaphyseal diameters of tarsal bone of pullets on week 5.

Crown-rump, radio-ulna and tibiotarsal lengths were greater (p<0.05) in IOIF compared to the EC (FIG. 16-18). All the length measurements were significantly lower in IF compared to the EC. IO did not vary with EC in crown-rump lengths, however, tibio-tarsal and radio-ulnar lengths were higher (p<0.05) in IO compared to the EC. Furthermore, the tibial bone weight was significantly higher (p<0.05) in IOIF (5.016±0.19 g) compared to the IF (4.902±0.2 g), IO (4.515±0.23 g) and EC (4.14±0.28 g; FIG. 15). Moreover, the epiphysial and diaphyseal tarsal bone diameters were measured, and the results show that in-feed probiotic supplementation has significantly improved bone growth post-hatch. Both diameters were larger by~30 mm in IF and IOIF compared to IO and EC (FIG. 19). For instance, in EC and IO, the epiphyseal diameters were ~4 cm compared to −4.4 in IOIF and IF; while the diaphyseal diameters were ~5 cm in EC and IO and ~5.3 cm in IF and IOIF (FIG. 16). This is significant. In this study, chicks with dietary probiotic supplementation (IF and IOIF) had higher body weight, RTC weight, breast weight and leg weight. In ovo probiotic supplementation (10) without in-feed supplementation did not exert a significant effect on body weight gain. In ovo probiotic supplementation resulted in an increased body length, especially radio-ulna and tibiotarsus. However, dietary supplementation alone was not sufficient to enhance Serum cholesterol (FIG. 20a) and triglyceride (FIG. 20b) levels were estimated from week 5 samples to study the effect of probiotics. Total cholesterol level (95 µg/dL) was significantly (p<0.05) more in IOIF and no significant difference was observed in HDL levels among different groups. LDL lipid level in IOIF (50 µg/dL) was significantly (p<0.05) higher compared to IF (25 µg/dL). Serum triglyceride level was 1 mmol/L in IO and 0.6 mmol/L in IOIF and were significantly different (p<0.05) from each other and from EC and IF (1.6-1.8 mmol/L). There is no study on the effect of in ovo probiotic supplementation on serum cholesterol and triglyceride levels. LDL, HDL and total cholesterol were lowest in IF group, however, we did not observe any significant difference in triglyceride levels compared to the control. Further, in ovo probiotic supplementation has reduced the triglyceride level compared to the control.

In conclusion, early in ovo probiotic administration enhanced the growth and development of the chicken embryo and hatchling and subsequently improved post-hatch growth in pullets. Specifically, the improvement in embryo and hatchling growth was associated with an improvement in post-hatch growth following in ovo probiotic supplementation (IO). This clearly demonstrates that improving embryonic growth can promote subsequent development in post-hatch birds even in the absence of in-feed probiotic supplementation (in ovo only). However, among the different treatment schemes, sustained probiotic application (IOIF) was found to be the most effective in promoting overall growth in hatchlings and pullets. Since, hatchling and pullet growth and development are critical to laying hen performance, in ovo and in-feed probiotic supplementation could potentially be employed as an alternative to AGP in layers.

Example 4: Effect of In Ovo Probiotic Supplementation on Muscle Development in Chicken Embryos This study analyzed the effect on embryonic myogenesis of spraying Ross 308 embryonated eggs with different probiotics.

Materials and Methods

LAB Culture Conditions and Preparation of Probiotic Spray

*Lactobacillus paracasei* DUP-13076, and *L. rhamnosus* NRRL-B- were grown in MRS broth at 37° C. overnight. After incubation, the cultures were centrifuged (3200×g, 12 min), and washed twice in PBS. The pellet was then resuspended in PBS and used as the inoculum. The probiotic cocktail was prepared by mixing equal portions of the two probiotics. The bacterial population in the inoculum was determined by standard dilution and plating on MRS agar, followed by incubation at 37° C. for 24 hours.

Experimental Design

Fertile Ross 308 broiler eggs (Myers Poultry Farm, LLC, South Fork, Pa.) were randomly assigned to the following four groups. A total of 120 eggs were used with 30 eggs per group were used for the study in four treatment groups. The 4 treatment groups will include: i) Egg control (EC; PBS only), ii) *Lactobacillus paracasei* DUP 13076 (LP) on eggs (eggs were sprayed with 200 µl (~9 log CFU/egg) on days 1, 3, 7, 10, 14, and 18 of incubation, iii) *L. rhamnosus* NRRL B-442 (LR) on eggs (eggs were sprayed with 200 µl (~9 log CFU/egg) on days 1, 3, 7, 10, 14, and 18 of incubation and iv) a cocktail of *Lactobacillus paracasei* DUP 13076 and *L. rhamnosus* NRRL B-442 (Cocktail) on eggs (eggs were sprayed with 200 µl (~9 log CFU/egg) probiotic cocktail on days 1, 3, 7, 10, 14, and 18 of incubation).

Muscle Collection

On day 10, 14 and 18 of incubation, pectoral muscle samples were collected from the embryos and processed as previously described (Reed et al., *Journal of animal science and biotechnology*, 5, 43 (2014a)). Briefly, for muscle histology, samples were frozen in liquid nitrogen, embedded in optimal cutting media (OCT), and stored at −80° C. until they were sectioned using a cryostat microtome to 10 µm sections of muscle tissue. Muscle samples for RT-qPCR were collected in 10 volumes of RNAlater solution and will be stored at −80° C. until further processing.

Immunohistochemistry and Imaging

Cross-sectional area and muscle fiber density were visualized by staining with wheat germ agglutinin (WGA, 1:50, Invitrogen, Carlsbad, Calif.). DAPI (4',6-diamidino-2-phenylindole) was used to visualize nuclei and muscle nuclei density was estimated. Muscle sections were fixed to slides for 1 minute on a hot plate and rehydrated in 4% paraformaldehyde for 20 min under darkness, followed by washing with PBS. Samples were incubated in WGA overnight in the dark in a humidified box at 4° C., followed by washing with PBS. Coverslips were placed on the slides with mounting medium with DAPI (EverBrite Mounting Medium with DAPI, Biotium, Fremont, Calif.). Imaging was performed using an Axiovert Widefield microscope (Zeiss, Jena, Germany) with 400× magnification. The figures were analyzed using ImageJ (NIH) software. Total of 60 images were used for treatment per time point which includes 5 technical replicates. Muscle cross-sectional area was determined by measuring the region of the fiber stained with WGA. Muscle fiber density and nuclei density also were determined by counting their numbers in an area of 1 µm².

RT-qPCR of Genes Involved in Myogenesis

Muscle samples for RNA extraction were collected at the respective sampling times in RNAlater and stored at −80° C. RNA will be isolated from muscle samples using RNeasy minikit (Qiagen, MD, USA) according to the manufacturer's protocol, and RNA quality check was performed using the Nanodrop (Eppendorf, CT, USA). cDNA was synthesized from the RNA using the iScript reverse transcriptase kit (BioRad, CA, USA). Specific primers for candidate genes (pax3, pax7, myf5, mrf4, fgfI, fgfIV, igfI, igfII, igfIR, igfIIR, myoD, myogenin, and myostatin.) were selected from published literature (Zammit et al., *Journal of Histochemistry & Cytochemistry* 54, 1177-1191 (2006) and RT-qPCR was performed on the StepOnePlus™ platform using the SYBR green assay (Applied Biosystems, CA, USA) under custom thermal cycling conditions. Duplicate samples were run from each biological sample and a total of six biological replicates from each treatment group were included in the assay. Data were normalized to the endogenous control (GAPDH), and comparative quantification ($2^{-\Delta\Delta CT}$) was carried out to detect changes in relative gene expression between the treatment groups and EC.

Statistical Analysis

The data were analyzed as a completely randomized design with repeated measures treatments arranged as a 4×4 factorial with treatments and time as main effects. Analyses were performed using the MIXED procedure in SAS. When appropriate, means comparisons will be made using the least square means and differences between least square means were separated. The significance was considered at $p<0.05$. For RT-qPCR assays, the data was analyzed using the PROC-MIXED procedure of SAS. The results of two independent tests were tested for significance at a p-value of $<0.05$ using MANOVA.

Results and Discussion

Figure 22:
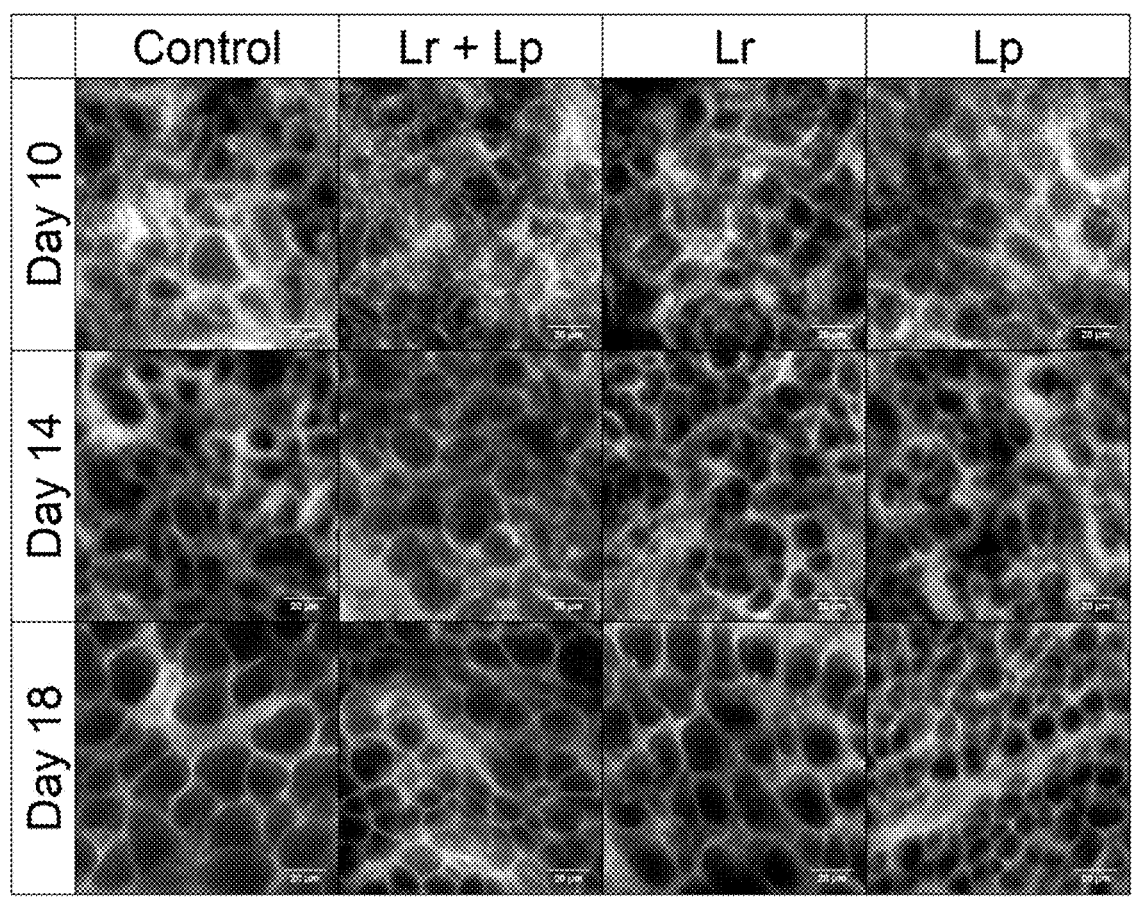
FIG. 22 is a photomicrograph showing breast muscle cross-sections from broiler embryos stained with WGA (gray) and mounted with DAPI (blue) with images captured at 600× total magnification; scale bars show 20 μm.
Figure 23:
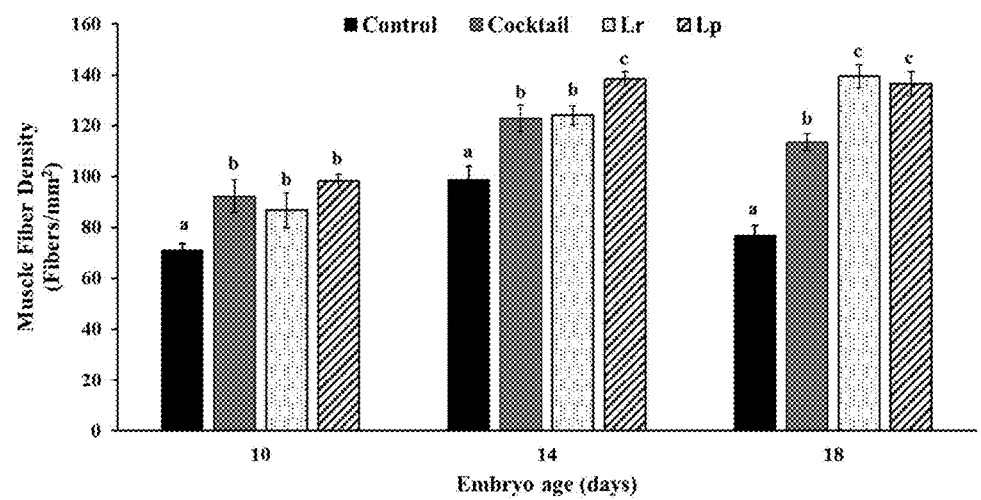
FIG. 23 is a bar graph showing influence of administration of the probiotic composition described herein on muscle fiber density in the pectoralis major muscle of broiler embryos.

Muscle fiber density is inversely related to muscle fiber cross section area. Hence, an increase in muscle fiber density (higher number of fibers in a given area) will be associated with a concomitant decrease in the CSA of the muscle fiber (smaller fibers; FIG. 22). Therefore, improvement in prenatal muscle growth and development would be linked to an increase in myofiber hyperplasia. As can be seen in FIG. 22, early supplementation of probiotics to embryonated chicken eggs significantly increased muscle hyperplasia when compared to the control ($p<0.05$). For instance, on day 18 of incubation, the fiber density in the treatment groups ranged from 113-139 fibers per mm² when compared to 76 fibers per mm² in the control (FIG. 23). Additionally, the increase in muscle development (increased fiber density) was sustained throughout embryonic growth starting from day 10-day 18 of incubation. More specifically, overall, probiotic treatments increased muscle fiber hyperplasia by 29% and 70% on day 10, 14, and day 18, respectively, when compared to the control.

Figure 24:
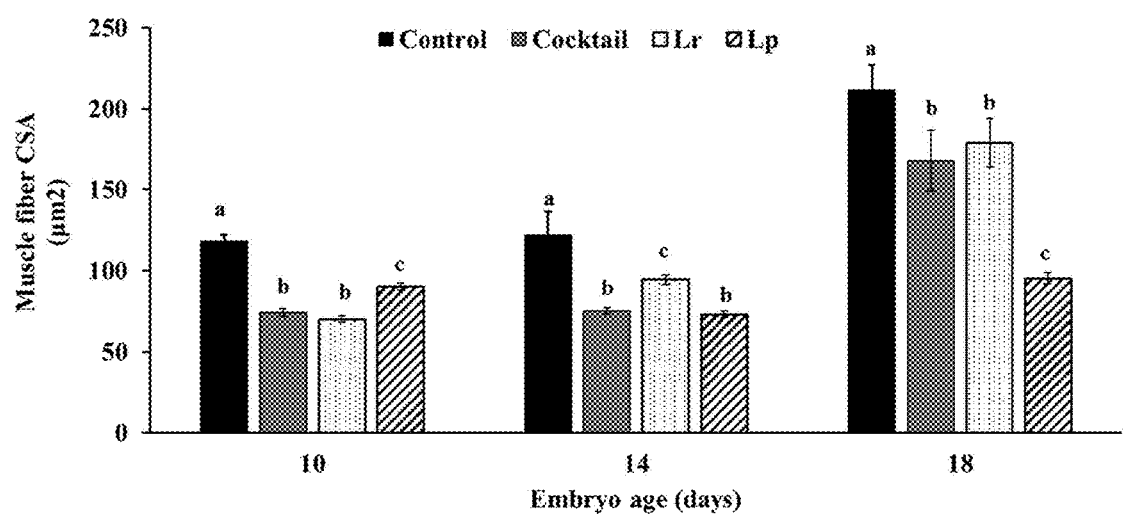
FIG. 24 is a bar graph showing the effect of administration of the probiotic composition described herein on mean cross-sectional are (CSA) of the pectoral muscle fibers in broiler embryos.

In the case of fiber CSA measurements, the control embryos consistently demonstrated significantly higher CSA when compared to the treatment groups ($p<0.05$). As seen in FIG. 24, with the control samples, the CSA of the muscle fibers on day 10, 14 and 18 was 118±3.94, 121.94±14.57, 211.41±15.67 µm², respectively. On the other hand, with the LP treatments, the CSA was observed to be 89±2.2 µm² on day 10, 73±2.05 µm² on day 14 and 95±3.28 µm² on day 18 when compared to the control. As previously described, the decrease in CSA was associated with an accompanying increase in fiber density (FIG. 22). Since muscle growth during embryonic life predominantly occurs through hyperplasia, the increase in myoblast cell number observed in our study implies a positive effect of probiotic supplementation on pre-natal muscle development.

During the embryonic period of muscle development, myoblasts are proliferating, differentiating into multinucleated myotubes, and forming muscle fibers. Since muscle fiber number is set at hatch, post-natal muscle development occurs via fiber hypertrophy. However, for this hypertrophy to occur, there must be an increase in protein synthesis, which is the direct consequence of more DNA resulting in increased transcription and translation. To acquire more DNA, there is a required increase in nuclei number. Just as with muscle fiber number, nuclei number derived from myoblasts is also set at hatch. Hence, to favor optimum muscle growth following hatch, there is a need to improve nuclei requirement during embryonic development. Therefore, given the potential effect that pre-hatch muscle growth can have on post-hatch muscle development, the effect of probiotic supplementation on myofiber nuclei number was determined.

Figure 25:
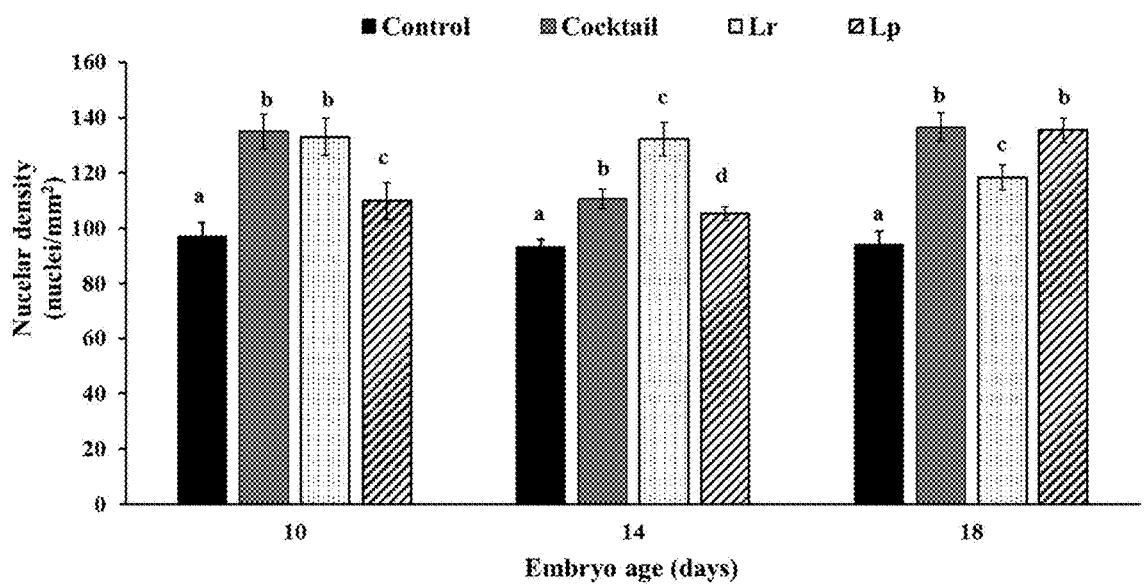
FIG. 25 is a bar graph showing the effect of administration of the probiotic composition described herein on myofiber nuclei density in the pectoral muscle fibers in broiler embryos.

The effect of early probiotic supplementation on myofiber nuclei number density is depicted in FIG. 25. As seen with muscle fiber density, application of probiotics significantly improved muscle fiber nuclei density when compared to the control (p<0.05). With the control samples, the nuclei density ranged from 94-97 per mm$^2$ throughout the incubation period. On the other hand, with the LP treatment group, the myofiber nuclei density was 109±6.72, 105.3±2.53 and 135±4.41 per mm$^2$ on day 10, 14 and 18 respectively. Similarly, with LR and cocktail treatments, the nuclei density was 133±6.67 and 135±6.28, 132±6.1 and 110±3.55 and 118±4.46 and 136±5.14 per mm$^2$ on day 10, 14 and 18 respectively. Overall, the nuclei density in the probiotic treatment groups was increased by 29-37% on day 10 and 18, respectively, when compared to the control.

In order to elucidate the mechanism by which probiotics improved muscle hyperplasia in the embryo, differential gene expression of key myogenic factors was investigated. Since application of a probiotic cocktail did not result in significantly different results when compared to the single strains, qPCR assay was only performed on muscle sections from embryos treated with LP and LR. Skeletal muscle development and satellite cell function is tightly regulated by a number of myogenic regulatory factors including myogenic determination factor I (MyoD), myogenin (MyoG), myogenic factor 5 (Myf5) and myogenic regulatory factor 4 (MRF4). Of these factors, Myf5 and MyoD play early roles in the determination of muscle precursor cells to the myogenic lineage. Although these are first expressed in proliferating myoblasts, evidence suggests that Myf5 functions more towards proliferation and MyoD prepares the myoblast for efficient differentiation. Overall, mrf4, myf5, and myoD commit cells to a myogenic program and are important for the formation of myotubes by the fusion of myocytes. As seen in Table 21, the relative expression of the myogenic factors, mrf4, myf5, myoD, and myoG was significantly lower in both treatment groups on day 10, and this could be due to early maturation of the myofiber in the treatment groups compared to the control. The results correlate with the muscle fiber density data, where muscle fiber density was greater in the probiotic-treated groups on day 10. On day 14, there was no significant difference in myoG expression, and expression of mrf4, myf5 and myoD was downregulated in both treatment groups. However, on day 18, all myogenic factors including mrf4, myf5, myoG and myoD were significantly upregulated in LR while mrf4 and myoD were downregulated in the LP-treated embryos (p<0.05). The results indicate that there may be early recruitment of precursor cells and faster differentiation in the myocytes with probiotic treatment on embryos.

TABLE 21

Relative fold change in gene expression profile of genes involved in myogenesis.

| Gene | Day 10 | | Day 14 | | Day 18 | |
|---|---|---|---|---|---|---|
| | LR | LP | LR | LP | LR | LP |
| fgf2 | −1.02 ± 0.051a | 1.02 ± 0.051a | −1.29 ± 0.0635b | 1.27 ± 0.128a | 2.56 ± 0.1085 b | 2.17 ± 0.13c |
| fgf4 | 1.15 ± 0.0575 a | 1.74 ± 0.087b | −1.12 ± 0.056a | −1.63 ± 0.0815c | 3.53 ± 0.1765b | 3.64 ± 0.182b |
| igf1 | 1.43 ± 0.0715b | 3.04 ± 0.152c | 1.35 ± 0.0675b | 1.34 ± 0.067b | 1.61 ± 0.0805b | 1.14 ± 0.057a |
| igf1R | 2.73 ± 0.1365b | 2.18 ± 0.109c | −1.63 ± 0.0815b | −1.13 ± 0.0565a | 3.60 ± 0.18b | −1.09 ± 0.0545a |
| mrf4 | −2.43 ± 0.1215b | −1.75 ± 0.0875b | −2.94 ± 0.147b | −2.04 ± 0.102c | 1.47 ± 0.0735b | −3.33 ± 0.1665c |
| myf5 | −8.33 ± 0.4165b | −6.66 ± 0.333c | −7.14 ± 0.357b | −3.44 ± 0.172c | 1.44 ± 0.072b | 1.56 ± 0.078c |
| myoD | −2.56 ± 0.128b | −2.12 ± 0.106c | −2.5 ± 0.125b | −1.96 ± 0.098c | 1.98 ± 0.099b | −1.16 ± 0.058a |
| Alyogenm (myoG) | −2.5 ± 0.125b | −1.58 ± 0.079b | 1.00 ± 0.05a | −1.16 ± 0.058a | 1.37 ± 0.0685b | 4.37 ± 0.2185c |

Values are expressed as mean ± SE. a-c: Different superscript indicate significant difference between control (a) and treatments within each sampling time. The gene expression of the control for each time point was considered as 1$^a$.

Besides the myogenic factors, myogenesis is also under the influence of growth factors including fibroblast growth factor (FGF), platelet-derived growth factor, growth hormone and insulin-like growth factor (IGF). Of these, IGF has been implicated in the control of skeletal muscle growth and development during embryogenesis, post-natal hypertrophy and regeneration. In case of broilers, recent research has demonstrated that these fast-growing birds may enhance myogenic determination and differentiation by upregulating the above-mentioned myogenic regulators both during embryonic and post-natal muscle growth. In the present study, when compared to the control, igf1 was significantly upregulated in both treatment groups at all the sampling time points, and that would stimulate both muscle cell proliferation and differentiation. Further, a significant increase in igf1R (IGF1 receptor) expression was also observed on day 10 and 18. With reference to FGF, fgf2 it regulates myogenesis by stimulating myoblast proliferation and inhibiting their differentiation. fgf4 has a similar function as that of fgf2, however, acts through a different mechanism of action. There was no significant change in fgf2 expression on day 10 treatment groups. However, it was significantly upregulated (2 fold increase) on day 18 indicating that myofiber differentiation may be inhibited and the muscle is maintained in a state of proliferation. A similar trend in expression was observed with fgf4 expression on day 18 (3 fold increase). This increase in expression of growth factors that play a role in muscle hyperplasia correlates with the increase in muscle fiber numbers observed in the probiotic-treated embryos.

Overall, early probiotic supplementation improved prenatal muscle development by increasing muscle fiber hyperplasia and nuclei density. Increased muscle fiber density by the time of hatch is significant for broiler production as it is expected to translate into increased muscle mass during post-natal development as fibers undergo protein accretion. Further, increased nuclei by the time of hatch are also expected to contribute to improved protein accretion during post-hatch. Also, supplementation of probiotics by spray application on fertile eggs is a non-invasive and user-friendly approach to improve growth in broilers. Moreover, egg spraying is a commonly employed method to disinfect hatching eggs prior to the setting. Hence, it is expected that spray application of probiotics on hatching eggs could be integrated with routine hatchery management practices.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure. All patents and publications referenced herein are hereby incorporated by reference in their entirety.

It is to be understood the invention is not limited to particular systems described which may, of course, vary. It is also to be understood that the terminology used herein is for the purpose of describing particular embodiments only, and is not intended to be limiting.

Further modifications and alternative embodiments of various aspects of the embodiments described in this disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as the presently preferred embodiments. Elements and materials may be substituted for those illustrated and described herein, parts and processes may be reversed, and certain features of the embodiments may be utilized independently, all as would be apparent to one skilled in the art after having the benefit of this description. Changes may be made in the elements described herein without departing from the spirit and scope of the following claims.

The invention claimed is:

1. A method for enhancing the growth of poultry comprising topically administering a first probiotic composition to a fertilized, unhatched poultry egg, wherein the first probiotic composition is administered to the egg at one or more predetermined time intervals after laying, wherein a first administration is applied prior to setting and a last administration is applied prior to hatching.

2. The method of claim 1, wherein, after the probiotic composition is administered, the egg is incubated and hatched.

3. The method of claim 1, wherein the probiotic composition comprises an aerosol composition, and the administration comprises spraying the surface of the egg.

4. The method of claim 1, wherein the probiotic composition comprises one or more bacteria, one or more fungi or mixtures of one or more bacteria and one or more fungi.

5. The method of claim 4, wherein the probiotic composition comprises one ore more bacteria and the one or more bacteria are lactic acid bacteria.

6. The method of claim 4, wherein the one or more bacteria are selected from the group consisting of *Bacillus, Lactobacillus, Lactococcus, Propionibacterium, Enterococcus, Pediococcus*, Baterioides, and *Bifidobacterium* and the one or more fungi are selected from the group consisting of *Saccharomyces* and *Aspergillus*.

7. The method of claim 4, wherein the probiotic composition comprises a mixture of bacteria and the bacteria are *Lactobacillus paracasei* and *L. rhamnosus*.

8. The method of claim 1, further comprising administering a second probiotic composition to a chick hatched from the egg, wherein the second probiotic composition is the same or different from the first probiotic composition.

9. The method of claim 8, wherein the second probiotic composition is administered to the chick orally.

10. The method of claim 9, wherein the probiotic composition is combined with feed.

11. The method of claim 8, wherein the enhanced growth is post-hatch growth.

12. The method of claim 11, wherein the post-hatch growth is an increase over control in post-hatch weight, ready-to-cook weight, breast weight and bone length.

13. The method of claim 1, wherein the poultry is selected from the group consisting of chicken, duck, and ostrich.

14. The method of claim 13, wherein the chicken is selected from the group consisting of layers and broilers.

15. The method of claim 1, wherein the enhanced growth is enhanced embryonic growth.

16. The method of claim 1, wherein the enhanced embryonic growth is an increase over control in embryo weight, crown rump length and/or muscle growth.

17. The method of claim 1, wherein the administration of the probiotic composition additionally enhances poultry performance.

18. The method of claim 17, wherein the poultry performance is increased yolk sac carbohydrate levels and/or increased hatchability.

* * * * *